US010067137B2

(12) United States Patent
Fu et al.

(10) Patent No.: US 10,067,137 B2
(45) Date of Patent: *Sep. 4, 2018

(54) MAGNETIC NANOCOMPOSITIONS FOR HIGHLY SENSITIVE MOLECULAR AND CELLULAR ENRICHMENT, PURIFICATION AND DETECTION

(71) Applicant: NVIGEN, INC., Sunnyvale, CA (US)

(72) Inventors: Aihua Fu, Sunnyvale, CA (US); Zheng Meng, Sunnyvale, CA (US)

(73) Assignee: NVIGEN, INC., Sunnyvale, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/389,376

(22) PCT Filed: Apr. 1, 2013

(86) PCT No.: PCT/US2013/034865
§ 371 (c)(1),
(2) Date: Sep. 30, 2014

(87) PCT Pub. No.: WO2013/149265
PCT Pub. Date: Oct. 3, 2013

(65) Prior Publication Data
US 2015/0212095 A1    Jul. 30, 2015

Related U.S. Application Data

(60) Provisional application No. 61/618,778, filed on Mar. 31, 2012.

(51) Int. Cl.
*G01N 33/58* (2006.01)
*G01N 33/543* (2006.01)

(52) U.S. Cl.
CPC ..... *G01N 33/587* (2013.01); *G01N 33/54326* (2013.01); *G01N 33/54346* (2013.01); *G01N 2446/86* (2013.01)

(58) Field of Classification Search
CPC .............................. G01N 33/587; G01N 33/58
See application file for complete search history.

(56) References Cited

U.S. PATENT DOCUMENTS 7,906,345 B2    3/2011   Wang et al.
8,722,017 B2 *  5/2014   Fu .................. A61K 49/0002
                                                424/9.32

(Continued)

FOREIGN PATENT DOCUMENTS

WO    2008-156510 A2    12/2008
WO    2010-076032 A1     7/2010

OTHER PUBLICATIONS

Kim et al., "Multifunctional Uniform Nanoparticles Composed of a Magnetite Nanocrystal Core and a Mesoporous Silica Shell for Magnetic Resonance and Fluorescence Imaging and for Drug Delivery", Angew. Chem. Int. Ed., vol. 47, pp. 8438-8441, published Aug. 25, 2008.*

(Continued)

*Primary Examiner* — Tracy Vivlemore
*Assistant Examiner* — Nam P Nguyen
(74) *Attorney, Agent, or Firm* — Jun He Law Offices P.C.; James J. Zhu

(57) ABSTRACT

The present invention relates to a nanocomposition capable of capturing or enriching an analyte at a sub-nanogram level and methods thereof. The nanocomposition can comprise a nanostructure operably linked to an analyte-capturing member.

7 Claims, 18 Drawing Sheets

(56) References Cited

U.S. PATENT DOCUMENTS

| | | | |
|---|---|---|---|
| 9,708,660 B2* | 7/2017 | Fu | C12Q 1/6876 |
| 9,711,266 B2* | 7/2017 | Fu | H01F 1/01 |
| 2002/0009759 A1* | 1/2002 | Terstappen | B03C 1/01 |
| | | | 435/7.23 |
| 2006/0118757 A1 | 6/2006 | Klimov et al. | |
| 2008/0093219 A1 | 4/2008 | Goldberg et al. | |
| 2010/0008862 A1* | 1/2010 | Fu | A61K 49/0002 |
| | | | 424/9.32 |
| 2015/0037249 A1* | 2/2015 | Fu | A61K 47/48861 |
| | | | 424/1.11 |
| 2015/0051102 A1* | 2/2015 | Fu | G01N 33/54326 |
| | | | 506/9 |
| 2015/0076392 A1* | 3/2015 | Fu | A61K 49/0002 |
| | | | 252/62.51 R |
| 2015/0252407 A1* | 9/2015 | Fu | C12Q 1/6806 |
| | | | 435/6.12 |
| 2016/0279270 A1* | 9/2016 | Fu | A61K 49/0002 |
| 2017/0015975 A1* | 1/2017 | Fu | C12N 5/0068 |

OTHER PUBLICATIONS

Sarawade et al., Preparation of Hydrophobic mesoporous silica powder with a high specific surface area by surface modification of a wet-gel slurry and spray-drying, Powder Technology, vol. 197, pp. 288-294, published Oct. 17, 2009.*

* cited by examiner

| (a) 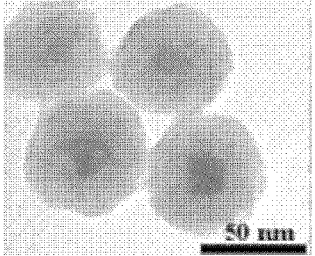 From Viswagen (www.viswagenbiotech.com) product description: TEM of nanoparticles containing magnetic core and silica shell component. This is for their products of magnetic and fluorescent nanoparticles. The silica structure is clearly observable under TEM. | (d) 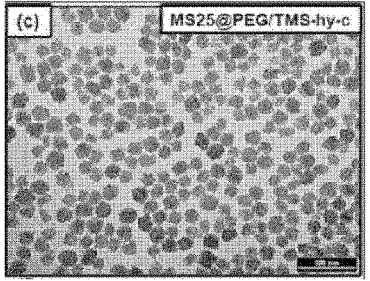 TEM micrograph of mesoporous silica nanoparticles synthesized from prof. Christy L. Hayne's group. The siliceous structure is clearly observable under TEM. (J. Am. Chem. Soc., 2011, 133, 20444-20457.) |
|---|---|
| (b) 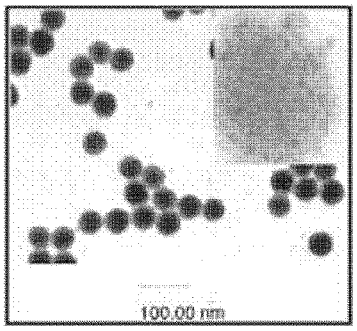 TEM micrograph of luminophore doped silica nanoparticles prepared by Prof. Weihong Tan's group. These silica nanoparticles could be clearly observed under TEM. (Anal. Chem. 2001, 73, 4988-4993.) | (e) 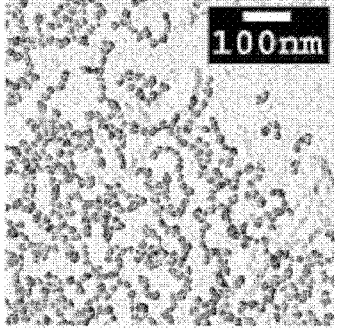 TEM micrograph of fluorescent silica nanoparticles by incorporating organic fluorophores within a siliceous structure from Prof. Ulrich Wiesner's group. the siliceous structure is clearly observable under TEM. (Nano letters, 2005, 5, 113.) |

Figure 3 (continued)

ELISA Test Magnetic Nanostructure-Protein A Conjugates Binding to EP20 Antibody

Sample 1: Mag-PA (2012-01-10), 100 ul + 0.1 ng EP20 antibody

Sample 2: Mag-PA (2012-01-10), 100 ul + 0.05 ng EP20 antibody

Sample 3: Mag-PA (2012-01-10), 100 ul + 0.02 ng EP20 antibody

Sample 4: Mag-PA (2012-01-10), 100 ul + 0.01 ng EP20 antibody

1: 0.1 ng antibody
2: 0.05 ng antibody
3: 0.02 ng antibody
4: 0.01 ng antibody, 1.25 pM

1: 0.01 ng antibody in 1.5 ml volume, 41.7 fM
2: 0.01 ng antibody in 10 ml volume, 6.25 fM

MAGNETIC NANOCOMPOSITIONS FOR HIGHLY SENSITIVE MOLECULAR AND CELLULAR ENRICHMENT, PURIFICATION AND DETECTION

CROSS-REFERENCE TO RELATED APPLICATIONS

The present application claims the benefit of U.S. Provisional Patent Application No. 61/618,778 filed on Mar. 31, 2012, which is incorporated herein by reference in its entirety.

BACKGROUND

Enrichment, purification and detection of analytes in biological samples at a sub-nanogram level have always been a challenge in research and development. Therefore, there are needs in continuing to develop novel systems and methods to achieve these purposes.

SUMMARY OF THE INVENTION

One aspect of the present disclosure relates to nanocompositions capable of capturing or enriching an analyte at a sub-nanogram level. In certain embodiments, the nanocomposition comprises a nanostructure operably linked to an analyte-capturing member.

In certain embodiments, the sub-nanogram level of an analyte is no more than 100 ng, 10 ng, 1 ng or 0.1 ng. For example, the sub-nanogram includes 0.01 ng, 0.02 ng. 0.03 ng, 0.04 ng, 0.05 ng, 0.06 ng, 0.07 ng, 0.08 ng, 0.09 ng, 0.1 ng, 0.2 ng, 0.3 ng, 0.4 ng, 0.5 ng, 0.6 ng, 0.7 ng, 0.8 ng, 0.9 ng, 1.0 ng, or any ranges between any of above mentioned level (e.g., between 0.01 ng and 100 ng, 0.01 ng and 10 ng, 0.01 ng and 1 ng, 0.01 ng and 0.1 ng).

In certain embodiments, the sub-nanogram level of an analyte is no more than 1000 pM, 100 pM, 10 pM, 1 pM, 0.1 pM, 0.01 pM, 0.001 pM (=1 fM) or 0.0001 pM. For example, the sub-nanogram includes 0.001 pM (=1 fM), 0.002 pM. 0.003 pM, 0.004 pM, 0.005 pM, 0.006 pM, 0.007 pM, 0.008 pM, 0.009 pM, 0.01 pM, 0.02 pM, 0.03 pM, 0.04 pM, 0.05 pM, 0.06 pM, 0.07 pM, 0.08 pM g, 0.09 pM, 0.1 pM, 0.1 pM, 0.2 pM, 0.3 pM, 0.4 pM, 0.5 pM, 0.6 pM, 0.7 pM, 0.8 pM, 0.9 pM, 1 pM, 2 pM, 3 pM, 4 pM, 5 pM, 6 pM, 7 pM, 8 pM, 9 pM, 10 pM or any ranges between any of above mentioned level (e.g., between 0.0001 pM and 1000 pM, 0.0001 pM and 100 pM, 0.0001 pM and 10 pM, 0.0001 pM and 1 pM, 0.0001 pM and 0.1 pM, 0.0001 pM and 0.01 pM, 0.0001 pM and 0.001 pM).

In certain embodiments, the sub-nanogram level of an analyte, in the case when the analyte is a biological sample, is a single sample (e.g., a cell), a plurality of samples (e.g., 2, 3, 4, 5, 6, 7, 8, 9, 10, 20, 30, 40, 50, 60, 70, 80, 90, 100, 200 samples).

In certain embodiments, the analyte specifically binds to the analyte-capturing member. In certain embodiments, the analyte-capturing member can be a Protein A, a Protein G, or an antigen binding member. In certain embodiments, the analyte can be an antibody that specifically binds to Protein A or Protein G, or an antigen that specifically binds to the antigen-binding member. In certain embodiments, the nanocomposition may further comprise an analyte specifically bound to the analyte capturing member.

In certain embodiments, the analyte is a cell, part of a cell or subcellular structure, a virus, an antibody, a protein/peptide, a nucleic acid; carbohydrate, lipid, a polymer, or a small organic molecule; a ligand, a receptor, a guest molecule, a host molecule, a circulating tumor cell, or a circulating DNA.

In certain embodiments, the nanostructure is a porous nanostructure which has been disclosed in U.S. Prov. Appl. 61/589,777 and U.S. patent application Ser. No. 12/460,009, both of which are incorporated herein in their entirety). In certain embodiments, the nanostructure comprises at least one core nanoparticle embedded in or coated with a low density porous 3-D structure or coating, which is capable of carrying or associating with at least one payload within or on the surface of the nanostructure.

In certain embodiments, the core nanoparticle comprises a nanoparticle or a cluster of nanoparticles. A single core nanoparticle may comprise a plurality or a cluster of mini-nanoparticles. The nanoparticles in the cluster may be made by the same composition, or different compositions.

In certain embodiments, the core nanoparticle comprises a magnetic material. In certain embodiments, the magnetic material is ferromagnetic, ferrimagnetic, paramagnetic materials, or superparamagnetic. In certain embodiments, the magnetic material is superparamagnetic iron oxide (SPIO).

In certain embodiments, the core nanoparticle may further comprises a non-SPIO nanoparticle. The non-SPIO nanparticles include, for example, metallic nanoparticles (e.g., gold or silver nanoparticles), a metal oxide nanoparticle, semi-conductor nanoparticle (e.g., quantum dots with individual or multiple components such as CdSe/ZnS, doped heavy metal free quantum dots or other semiconductor quantum dots); polymeric nanoparticles (e.g., particles made of one or a combination of PLGA (poly(lactic-co-glycolic acid), PCL (polycaprolactone), PEG (poly ethylene glycol) or other polymers); siliceous nanoparticles; and non-SPIO magnetic nanoparticles (e.g., $MnFe_2O_4$, SAF, and other types of magnetic nanoparticles).

The core nanoparticle has a diameter ranging from about 1 nm to about 900 nm (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size).

In certain embodiments, the core nanoparticle has a shape of sphere, rod, tetrapod, pyramidal, multi-armed, nanotube, nanowire, nanofiber, or nanoplate.

In certain embodiments, the low density, porous 3-D structure refers to a structure with density at least 10 s times (e.g. 10 s times, 20 s times, 30 s times, 50 s times, 70 s times, 100 s times, 1000 s times, 10,000 times) lower than existing mesoporous materials (e.g. mesoporous materials having a pore size ranging from 2 nm to 50 nm). In certain embodiments, the low density, porous 3-D structure has a density of <1.0 g/cc (e.g. from 0.01 mg/cc to 1000 mg/cc). In certain embodiments, the density is determined using dry mass of the 3-D structure divided by the total volume of such 3-D structure in an aqueous solution.

In certain embodiments, the low density, porous 3-D structure is highly porous. Such low density structure further refers to a structure having at least 40% to at least 99.9% (preferably 50% to 99.9%) of empty space or porosity in the structure. In certain embodiments, at least 80% of the pores having size of 1 nm to 500 nm in pore radius.

In certain embodiments, the low density, porous 3-D structure is a structure that can not be obviously observed or substantially invisible under transmission electron microscope, for example, even when the feature size of the low density structure is in the 10 s or 100 s nanometer range.

In certain embodiments, the low density, porous 3-D structure is made of silicon-containing molecules (e.g., silanes, organosilanes, alkoxysilanes, silicates and derivatives thereof). For example, the silicon-containing molecules can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis[3-(triethoxysilyl) propyl]-tetrasulfide, Bis-[3-(triethoxysilyl) propyl]-disulfide, aminopropyltriethoxysilane, N-2-(aminoethyl)-3-amino propyltrimethoxysilane, Vinyltrimethoxysilane, Vinyl-tris(2-methoxyethoxy) silane, 3-methacryloxypropyl-trimethoxy silane, 2-(3,4-epoxycyclohexy)-ethyl trimethoxysilane, 3-glycidoxy-propyltriethoxysilane, 3-isocyanato-propyltriethoxysilane, 3-cyanatopropyltriethoxysilane, and sodium silicates.

In certain embodiments, the low density, porous 3-D structure is associated with the core nanoparticle via intra-molecular interaction (e.g. covalent bonds, metallic bonds, and/or ionic bonding) or inter-molecular interaction (e.g. hydrogen bond, and/or non covalent bonds).

In certain embodiments, the low density, porous 3-D structure is a stable crosslinked coating with thickness ranging from 1 nm to 1000 nm (e.g. from 1 nm to 500 nm). In certain embodiments, the thickness of the low density, porous 3-D structure is controllable, so is the number of payloads that could be carried.

In certain embodiments, the nanostructure is capable of carrying or being associated with one or more payloads. In certain embodiments, the payloads to be carried or associated with the nanostructure include, but are not limited to, a detectable agent (e.g. a fluorescent molecule, a chemoluminescent molecule, a bio-luminescent molecule, a radio-isotope, a MRI contrast agent, a CT contrast agent, an enzyme-substrate label, and/or a coloring agent), a targeting moiety (e.g. an antibody, an antigen, a ligand, an aptamer, a peptide, a nucleic acid, a polynucleotide, a polysaccharide, sugar, fatty acid, steroids, pyrimidines, and/or a hapten), a binding partner (e.g. antigen, antibody, receptor, ligand, DNA, RNA, peptide, aptamer, biotin, avidin, streptavidin, lectin, carbohydrate, Protein A, antibody Fc, desthiobiotin, and/or iminobiotin), a biological active agent (e.g. therapeutic agents, proteins, antibodies, peptides, nucleic acids, enzymes, thermal-responsive molecules, optical-responsive molecules, electronic-responsive molecules, magnetic-responsive molecules, pH-responsive molecules, enzymatic responsive molecules and/or chemical compounds), a drug, a therapeutic agent, a radiological agent, a chemological agent, a small molecule drug, a biological drug (e.g., peptides, proteins, antibodies, antigens, nucleic acids, aptamers and the like) and combinations thereof, which can be used to image, detect, study, monitor, evaluate, screen a disease, condition, and/or related biological event. In certain embodiments, the nanostructure comprises a first payload and a second payload. In certain embodiments, a payload can be an analyte-capturing member.

Another aspect of the present disclosure relates to methods of capturing, enriching, purifying, detecting or measuring an analyte in a sample at a sub-nanogram level, comprising the steps of: a) contacting the sample with a nanocomposition disclosed herein to form a mixture solution and allowing the binding of the analyte with the nanocomposition, b) applying a magnetic field to the mixture, and c) evaluating the presence of or absence of an analyte.

In certain embodiments, the method further comprises a step of removing liquid from the mixture solution in the presence of the magnetic field.

In certain embodiments, the method further comprises a step of washing the nanocomposition in the presence of magnetic field after removing the liquid and before eluting so as to remove un-bounded sample or un-bounded nanocompositions.

In certain embodiments, the method further comprises a step of eluting the analyte from the nanocomposition, and collecting the analyte from the nanocomposition in the presence of a magnetic field, for example, by applying an elution buffer.

In certain embodiments, the method further comprises a step of analyzing the eluate by detecting the presence of the analyte or quantifying the amount of the analyte.

In certain embodiments, an increase in the ratio and/or an increase in nanostructure facilitates the separation, purification or isolation.

Another aspect of the present disclosure relates to methods of determining whether a test agent in a sample specifically binds to an analyte and determine the nature of the agent, comprising the steps of: a) contacting the sample containing an analyte with a nanocomposition to form a mixture solution and allowing the binding of the agent with the nanocomposition, b) applying a magnetic field to the mixture, and c) evaluating whether there is a test agent binding to the analyte.

In certain embodiments, the method further comprises a step of removing liquid from the mixture solution in the presence of the magnetic field.

In certain embodiments, the method further comprises a step of washing the nanocomposition in the presence of magnetic filed after removing the liquid and before eluting.

In certain embodiments, the method further comprises a step of eluting the test agent from the nanocomposition and analyte, and analyzing the nature of the test agent, if the agent is present in the sample and binds to the analyte.

Another aspect of the present disclosure relates to a method of selecting or capturing an analyte (e.g., a cell) comprising the steps of determining and applying a ratio of nanocompositions per said analyte and mixing the nanocompositions with said analyte based on the ratio. In certain embodiments, the method increases the chance and/or amount of analytes captured.

Another aspect of present disclosure relates to a method of selecting or capturing an analyte (e.g., a cell) with a desired feature comprising the steps of mixing a nanocompositions with a sample, evaluating the number of nanocompositions binding to one said analyte, and selecting the analyte having the desired feature; wherein the desired feature includes more than or less than a certain number of nanocomposition binding to one analyte.

DESCRIPTION OF THE DRAWINGS

As shown in FIG. 11, 0.01 ng of EP20 antibody (in 50 ul solution) can be detected.

DETAILED DESCRIPTION OF THE INVENTION

Figure 1:
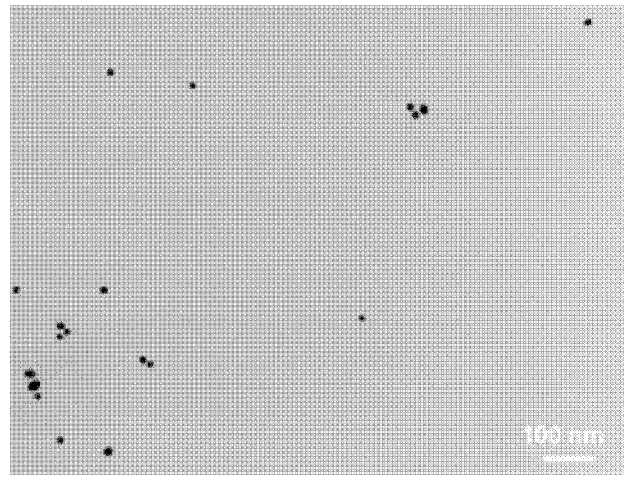
FIG. 1. An exemplary TEM image of silanized Au nanoparticles with core size of Au at ~20 nm and hydrodynamic size ~60 nm. No siliceous coating is visible from the TEM.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, solid state chemistry, inorganic chemistry, organic chemistry, physical chemistry, analytical chemistry, materials chemistry, biochemistry, biology, molecular biology, recombinant DNA techniques, pharmacology, imaging, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

The following embodiments are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Nanocomposition

One aspect of the present disclosure relates to a nanocomposition capable of capturing or enriching an analyte at a sub-nanogram level.

The term "analyte" as used herein refers to a sample that are desired to be captured, enriched, purified, detected or quantified. Examples of analyte include, without limitation, a molecule, a chemical, a compound, a biological sample, a cell, a virus, a bacteria, an antibody, a protein/peptide, a nuclei acid (DNA or RNA, fragment thereof, an oligonucleotide, complimentary to the capturing member nuclei acid); carbohydrate, lipid, a polymer, or a small organic molecule such as a drug; a ligand that specifically binds to a receptor as an analyte-capturing member, a receptor that specifically binds to a ligand as an analyte-capturing member, a guest molecule that specifically interacts with a host molecule or vice versa.

In certain embodiments, the analyte is part of a cell or subcellular structure, such as membrane proteins or markers of cells, vesicles or exosomes. The nanocompositions can access and/or bind the analyte cells, vesicles, or exosomes that are otherwise not accessible to other types of large magnetic beads.

In certain embodiments, the term "sub-nanogram level" refers to no more than 100 ng, 10 ng, 1 ng or 0.1 ng of an analyte. For example, the sub-nanogram includes 0.01 ng, 0.02 ng. 0.03 ng, 0.04 ng, 0.05 ng, 0.06 ng, 0.07 ng, 0.08 ng, 0.09 ng, 0.1 ng, 0.2 ng, 0.3 ng, 0.4 ng, 0.5 ng, 0.6 ng, 0.7 ng, 0.8 ng, 0.9 ng, 1.0 ng, or any ranges between any of above mentioned level (e.g., between 0.01 ng and 100 ng, 0.01 ng and 10 ng, 0.01 ng and 1 ng, 0.01 ng and 0.1 ng).

In certain embodiments, the sub-nanogram level means no more than 1000 pM, 100 pM, 10 pM, 1 pM, 0.1 pM, 0.01 pM, 0.001 pM (=1 fM) or 0.0001 pM of an analyte. For example, the sub-nanogram includes 0.001 pM (=1 fM), 0.002 pM. 0.003 pM, 0.004 pM, 0.005 pM, 0.006 pM, 0.007 pM, 0.008 pM, 0.009 pM, 0.01 pM, 0.02 pM, 0.03 pM, 0.04 pM, 0.05 pM, 0.06 pM, 0.07 pM, 0.08 pM, 0.09 pM, 0.1 pM, 0.1 pM, 0.2 pM, 0.3 pM, 0.4 pM, 0.5 pM, 0.6 pM, 0.7 pM, 0.8 pM, 0.9 pM, 1 pM, 2 pM, 3 pM, 4 pM, 5 pM, 6 pM, 7 pM, 8 pM, 9 pM, 10 pM or any ranges between any of above mentioned level (e.g., between 0.0001 pM and 1000 pM, 0.0001 pM and 100 pM, 0.0001 pM and 10 pM, 0.0001 pM and 1 pM, 0.0001 pM and 0.1 pM, 0.0001 pM and 0.01 pM, 0.0001 pM and 0.001 pM).

In certain embodiments, the sub-nanogram level of an analyte, in the case when the analyte is a biological sample, is a single sample (e.g., a cell), a plurality of samples (e.g., 2, 3, 4, 5, 6, 7, 8, 9, 10, 20, 30, 40, 50, 60, 70, 80, 90, 100, 200 samples). For instance, the anlyate to be enriched or captured is a cell, and the sub-nanogram level is a single cell or a plurality of cells.

The nanocomposition used herein comprises a nanostructure operably linked to an analyte-capturing member.

The term "operably linked" as used herein, includes embedding, incorporating, integrating, binding, attaching combining, cross-linking, mixing, and/or coating the analyte-capturing member to that the nanostructure. The analyte-capturing member can be operably linked to the nanostructure through non-covalent association (e.g. hydrogen bonds, ionic bonds, van der Waals forces, and hydrophobic interaction) or covalent binding. For example, the analyte-capturing member mixed with and/or incorporated onto the surface of the nanostructure, or can also be loaded to the pores of the nanostructure.

Analyte-Capturing Member

In certain embodiments, the analyte-capturing members (or analyte-binding members) are molecules capable of capturing or specifically binding to an analyte. "Capturing", "binding" or "specifically binding" as used herein, means that a non-random binding interaction between two molecules. The specific binding can be characterized by binding affinity (Kd), which is calculated as the ratio of dissociation rate to association rate (koff/kon) when the binding between the two molecules reaches equilibrium. The dissociation rate (koff) measured at the binding equilibrium may also be used when measurement of kon is difficult to obtain, for example, due to aggregation of one molecule. The analyte-binding affinity (e.g., KD or koff) can be appropriately determined using suitable methods known in the art, including, for example, Biacore (see, for example, Murphy, M. et al, Current protocols in protein science, Chapter 19, unit 19.14, 2006) and Kinexa techniques (see, for example, Darling, R. J., et al, Assay Drug Dev. Technol., 2(6): 647-657 (2004)).

Examples of analyte-capturing members include Protein A; Protein G; antigen-binding members (e.g., antibodies or fragments thereof); nucleic acid (or a fragment of nucleic acid, an oligo nucleotide); or a protein/peptide binding specifically to a molecule such as another protein/peptide, an antibody, a piece of nucleic acid (DNA or RNA), carbohydrate, lipid, a polymer, or a small organic molecule such as a drug; a ligand (e.g., a peptide, small molecule, hormone, a drug, toxin, neurotransmitter) that specifically binds to a receptor, or a receptor that specifically binds to a ligand, a chemical in a supermolecular structure (e.g., host-guest chemistry complex such as a p-xylylenediammonium bound within a cucurbituril) whereas the chemical is a host molecule (e.g., cyclodextrins, calixarenes, cucurbiturils, porphyrins, metallacrowns, crown ethers, zeolites, cyclotriveratrylenes, cryptophanes and carcerands) or a guest molecule (e.g., prostaglandin, itraconazole).

Protein A is an affinity ligand for an antibody having an immunoglobulin Fc domain, and can be useful in purification of antibodies that are based on human .gamma.1, .gamma.2, or .gamma.4 heavy chains (Lindmark et al., J. Immunol. Meth. 62:1-13 (1983)). Similarly, protein G is recommended for specific binding to antibodies of all mouse isotypes and for antibodies based on human .gamma 3 heavy chains (Guss et al., EMBO J. 5:1567 1575 (1986)). Avidin (or streptavdin) and biotin can specifically bind to each other to form strong and specific non-covalent association. An antigen binding member can be an antibody, an antibody fragment or an antibody memetics, such as, for example, scFV, Fab, Fab', Fv, single domain antibody, diabody, nanobody, domain antibody, dsFv, or canelized antibody. The antibodies or fragments can be polyclonal, monoclonal, of animal origin (e.g., murine, rabbit, camel), of human origin (e.g., fully human), chimeric, humanized, variable regions, CDRs, ScFv, bispecific, diabody, or other forms of antibodies with antigen-binding capabilities. In certain embodiments, the antibodies or antigen-binding fraction thereof specifically binds to a biomarker or biomarkers such as a specific antigen of a cancer cell or a stem cell or a cell of interest.

In certain embodiments, the analyte-capturing members may be physically absorbed into the nanostructure or covalently linked to the nanostructure through functional groups disclosed herein. In certain embodiments, the analyte-capturing members are operably linked to the nanostructure on its surface, so that the analyte capturing members would be accessible by the analyte.

In certain embodiments, the analyte is a substance that specifically interacts or binds to the analyte-capturing member. Example of analytes include a sample, a biological sample, a cell (e.g. an antibody producing hybridoma cell, a circulating tumor cell, a cell expressing a disease marker, etc.), a virus, an antibody, a protein/peptide, a nucleic acid (DNA or RNA, fragment thereof, an oligonucleotide, complimentary to the capturing member nucleic acid); carbohydrate, lipid, a polymer, or a small organic molecule such as a drug; a ligand that specifically binds to a receptor as an analyte-capturing member, a receptor that specifically binds to a ligand as an analyte-capturing member, a guest molecule that specifically interacts with a host molecule or vice versa, antibodies (e.g. those specifically bind to Protein A or G), antigens (e.g. those that specifically bind to antigen-binding members), nucleic acid (e.g. those that specifically bind to antibodies like in Chromatin immunoprecipitation), proteins and protein complexes (e.g. those that in immunoprecipitation or co-immunoprecipitations.).

A nanostructure can be operably linked to a suitable amount of the analyte capturing member. The ratio of the nanostructure to the analyte capturing member can be appropriately adjusted by people skilled in the art according to the specific needs. For example, the ratio of the nanostructures to the analyte capturing member can be increased for detection of a low amount of the analyte.

In certain embodiments, the nanocomposition may further comprise an analyte specifically bound to the analyte capturing member. In certain embodiments, the analyte can be eluted from the nanocomposition.

Nanostructure

The term "nanostructure" as used herein, refers to a particle having a diameter ranging from about 1 nm to about 1500 nm (e.g. from 1 nm to 1200 nm, from 1 nm to 1000 nm, from 1 nm to 800 nm, from 1 nm to 500 nm, from 1 nm to 400 nm, etc.). In certain embodiments, the nanostructure comprises a single particle or a cluster of particles. In certain embodiments, the nanostructure comprises a core nanoparticle and a coating. The core nanoparticle can be a single or a cluster of particles. The coating can be any coating known in the art, for example, a polymer coating such as polyethylene glycol, silane, and polysaachrides (e.g. dextran and its derivatives).

The nanostructures provided herein have a magnetic property or contain a magnetic material. Suitable magnetic materials include, for example, ferrimagnetic or ferromagnetic materials (e.g., iron, nickel, cobalt, some alloys of rare earth metals, and some naturally occurring minerals such as lodestone), paramagnetic materials (such as platinum, aluminum), and superparamagnetic materials (e.g., superparamagnetic iron oxide or SPIO).

The magnetic material has magnetic property which allows the nanostructure to be pulled or attracted to a magnet or in a magnetic field. Magnetic property can facilitate manipulation (e.g., separation, purification, or enrichment) of the nanostructures using magnetic interaction. The magnetic nanostructures can be attracted to or magnetically guided to an intended site when subject to an applied magnetic field, for example a magnetic field from high-filed and/or high-gradient magnets. For example, a magnet or a magnetic grid can be placed in the proximity of the nanostructures so as to attract the magnetic nanostructures. Magnetic field can also be formed through electromagensim (e.g., a solenoid carrying current).

In certain embodiments, the nanostructure provided herein comprises a magnetic nanoparticle which comprises a magnetic material. For example, the magnetic nanoparticle of the nanostructure is a superparamagnetic iron oxide (SPIO) nanoparticle.

The SPIO nanoparticle is an iron oxide nanoparticle, either maghemite ($\gamma$-$Fe_2O_3$) or magnetite ($Fe_3O_4$), or nanoparticles composed of both phases. The SPIO can be synthesized with a suitable method and dispersed as a colloidal solution in organic solvents or water. Methods to synthesize the SPIO nanoparticles are known in the art (see, for example, Morteza Mahmoudi et al, Superparamagnetic Iron Oxide Nanoparticles: Synthesis, Surface Engineering, Cytotoxicity and Biomedical Applications, published by Nova Science Pub Inc, 2011). In one embodiment, the SPIO nanoparticles can be made through wet chemical synthesis methods which involve co-precipitation of $Fe^{2+}$ and $Fe^{3+}$ salts in the presence of an alkaline medium. During the synthesis, nitrogen may be introduced to control oxidation, surfactants and suitable polymers may be added to inhibit agglomeration or control particle size, and/or emulsions (such as water-in-oil microemulsions) may be used to modulate the physical properties of the SPIO nanoparticle (see, for example, Jonathan W. Gunn, The preparation and characterization of superparamagnetic nanoparticles for biomedical imaging and therapeutic application, published by ProQuest, 2008). In another embodiment, the SPIO nanoparticles can be generated by thermal decomposition of iron pentacarbonyl, alone or in combination with transition metal carbonyls, optionally in the presence of one or more surfactants (e.g., lauric acid and oleic acid) and/or oxidatants (e.g., trimethylamine-N-oxide), and in a suitable solvent (e.g., dioctyl ether or hexadecane) (see, for example, US patent application 20060093555). In another embodiment, the SPIO nanoparticles can also be made through gas deposition methods, which involves laser vaporization of iron in a helium atmosphere containing different concentrations of oxygen (see, Miller J. S. et al., Magnetism: Nanosized magnetic materials, published by Wiley-VCH, 2002). In certain embodiments, the SPIO nanoparticles are those disclosed in US patent application US20100008862.

In certain embodiments, the nanostructure herein can be a non-SPIO nanoparticle.

The non-SPIO nanoparticles can be prepared or synthesized using suitable methods known in the art, such as for example, sol-gel synthesis method, water-in-oil micro-emulsion method, gas deposition method and so on. For example, gold nanoparticles can be made by reduction of chloroaurate solutions (e.g., $HAuCl_4$) by a reducing agent such as citrate, or acetone dicarboxulate. For another example, CdS semiconductor nanoparticle can be prepared from $Cd(ClO_4)_2$ and $Na_2S$ on the surface of silica particles. For another example, II-VI semiconductor nanoparticles can be synthesized based on pyrolysis of organometallic reagents such as dimethyl cadmium and trioctylphosphine selenide, after injection into a hot coordinating solvent (see, e.g., Günter Schmid, Nanoparticles: From Theory to Application, published by John Wiley & Sons, 2011). Doped heavy metal free quantum dots, for example Mn-doped ZnSe quantum dots can be prepared using nucleation-doping strategy, in which small-sized MnSe nanoclusters are formed as the core and ZnSe layers are overcoated on the core under high temperatures. For another example, polymeric nanoparticles can be prepared by emulsifying a polymer in a two-phase solvent system, inducing nanosized polymer droplets by sonication or homogenization, and evaporating the organic solvent to obtain the nanoparticles. For another example, siliceous nanoparticles can be prepared by sol-gel synthesis, in which silicon alkoxide precursors (e.g., TMOS or TEOS) are hydrolyzed in a mixture of water and ethanol in the presence of an acid or a base catalyst, the hydrolyzed monomers are condensed with vigorous stirring and the resulting silica nanoparticles can be collected. For another example, SAFs, a non-SPIO magnetic nanoparticle, can be prepared by depositing a ferromagenetic layer on each of the two sides of a nonmagnetic space layer (e.g., ruthenium metal), along with a chemical etchable copper release layer and protective tantalum surface layers, using ion-bean deposition in a high vacuum, and the SAF nanoparticle can be released after removing the protective layer and selective etching of copper.

The size of the nanoparticles ranges from 1 nm to 100 nm in size (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size). The size of nanoparticles can be controlled by selecting appropriate synthesis methods and/or systems. For example, to control the size of nanoparticles, synthesis of nanoparticles can be carried out in a polar solvent which provides ionic species that can adsorb on the surface of the nanoparticles, thereby providing electrostatic effect and particle-particle repulsive force to help stabilize the nanoparticles and inhibit the growth of the nanoparticles. For another example, nanoparticles can be synthesized in a micro-heterogeneous system that allows compartmentalization of nanoparticles in constrained cavities or domains. Such a micro-heterogeneous system may include, liquid crystals, mono and multilayers, direct micelles, reversed micelles, microemulsions and vesicles. To obtain nanoparticles within a desired size range, the synthesis conditions may be properly controlled or varied to provide for, e.g., a desired solution concentration or a desired cavity range (a detailed review can be found at, e.g., Vincenzo Liveri, Controlled synthesis of nanoparticles in microheterogeneous systems, Published by Springer, 2006).

The shape of the nanoparticles can be spherical, cubic, rod shaped (see, e.g., A. Fu et al., *Nano Letters,* 7, 179-182 (2007)), tetrapo-shaped (see, e.g., L. Manna et al., *Nature Materials,* 2, 382-385 (2003)), pyramidal, multi-armed, nanotube, nanowire, nanofiber, nanoplate, or any other suitable shapes. Methods are known in the art to control the shape of the nanoparticles during the preparation (see, e.g., Waseda Y. et al., Morphology control of materials and nanoparticles: advanced materials processing and characterization, published by Springer, 2004). For example, when the nanoparticles are prepared by the bottom-up process (i.e. from molecule to nanoparticle), a shape controller which adsorbs strongly to a specific crystal plane may be added to control the growth rate of the particle.

A single nanostructure may comprise a single nanoparticle or a plurality or a cluster of mini-nanoparticles (A. Fu et al., *J. Am. chem. Soc.* 126, 10832-10833 (2004), J. Ge et al., *Angew. Chem. Int. Ed.* 46, 4342-4345 (2007), Zhenda Lu et al., *Nano Letters* 11, 3404-3412 (2011).). The mini-nanoparticles can be homogeneous (e.g., made of the same composition/materials or having same size) or heterogeneous (e.g., made of different compositions/materials or having different sizes). A cluster of homogeneous mini-nanoparticles refers to a pool of particles having substantially the same features or characteristics or consisting of substantially the same materials. A cluster of heterogeneous mini-nanoparticles refers to a pool of particles having different features or characteristics or consisting of substantially different materials. For example, a heterogeneous mini-nanoparticle may comprise a quantum dot in the center and a discrete number of gold (Au) nanocrystals attached to the quantum dot. When the nanoparticles are associated with a coating (as described below), different nanoparticles in a heterogeneous nanoparticle pool do not need to associate with each other at first, but rather, they could be individually and separately associated with the coating.

In certain embodiments, a nanostructure disclosed comprises a plurality of nanoparticles. For example, the nanostructure contains 2, 3, 4, 5, 6, 7, 8, 9, 10, 11, 12, 13, 14, 15, 16, 17, 18, 19, 20, 25, 30, 35, 40, 50, 60, 70, 80, 90, 100, 100 s or 1000 s nanoparticles.

In certain embodiments, the nanostructure provided herein further comprises a coating. At least one core nanoparticle can be embedded in or coated with the coating. Any suitable coatings known in the art can be used, for example, a polymer coating and a non-polymer coating.

The coating interacts with the core nanoparticles through 1) intra-molecular interaction such as covalent bonds (e.g., Sigma bond, Pi bond, Delta bond, Double bond, Triple bond, Quadruple bond, Quintuple bond, Sextuple bond, 3c-2e, 3c-4e, 4c-2e, Agostic bond, Bent bond, Dipolar bond, Pi backbond, Conjugation, Hyperconjugation, Aromaticity, Hapticity, and Antibonding), metallic bonds (e.g., chelating interactions with the metal atom in the core nanoparticle), or ionic bonding (cation π-bond and salt bond), and 2) intermolecular interaction such as hydrogen bond (e.g., Dihydrogen bond, Dihydrogen complex, Low-barrier hydrogen bond, Symmetric hydrogen bond) and non covalent bonds (e.g., hydrophobic, hydrophilic, charge-charge, or π-stacking interactions, van der Waals force, London dispersion force, Mechanical bond, Halogen bond, Aurophilicity, Intercalation, Stacking, Entropic force, and chemical polarity).

In certain embodiments, the coating comprises a low density, porous 3-D structure, as disclosed in U.S. Prov. Appl. 61/589,777 and U.S. patent application Ser. No. 12/460,007 (all references cited in the present disclosure are incorporated herein in their entirety).

The low density, porous 3-D structure refers to a structure with density much lower (e.g., 10 s times, 20 s times, 30 s times, 50 s times, 70 s times, 100 s times) than existing mesoporous nanoparticles (e.g., mesoporous nanoparticles having a pore size ranging from 2 nm to 50 nm). (A. Vincent, et. al., J. Phys. Chem. C, 2007, 111, 8291-8298. J. E. Lee, et. al., J. Am. Chem. Soc., 2010, 132, 552-557. Y.-S. Lin, et. al., J. Am. Chem. Soc., 2011, 133, 20444-20457. Z. Lu, Angew. Chem. Int. Ed., 2010, 49, 1862-1866.)

In certain embodiments, the low density, porous 3-D structure refers to a structure having a density of <1.0 g/cc (e.g., <100 mg/cc, <10 mg/cc, <5 mg/cc, <1 mg/cc, <0.5 mg/cc, <0.4 mg/cc, <0.3 mg/cc, <0.2 mg/cc, or <0.1 mg/cc) (for example, from 0.01 mg/cc to 10 mg/cc, from 0.01 mg/cc to 8 mg/cc, from 0.01 mg/cc to 5 mg/cc, from 0.01 mg/cc to 3 mg/cc, from 0.01 mg/cc to 1 mg/cc, from 0.01 mg/cc to 1 mg/cc, from 0.01 mg/cc to 0.8 mg/cc, from 0.01 mg/cc to 0.5 mg/cc, from 0.01 mg/cc to 0.3 mg/cc, from 0.01 mg/cc to 1000 mg/cc, from 0.01 mg/cc to 915 mg/cc, from 0.01 mg/cc to 900 mg/cc, from 0.01 mg/cc to 800 mg/cc, from 0.01 mg/cc to 700 mg/cc, from 0.01 mg/cc to 600 mg/cc, from 0.01 mg/cc to 500 mg/cc, from 0.1 mg/cc to 800 mg/cc, from 0.1 mg/cc to 700 mg/cc, from 0.1 mg/cc to 1000 mg/cc, from 1 mg/cc to 1000 mg/cc, from 5 mg/cc to 1000 mg/cc, from 10 mg/cc to 1000 mg/cc, from 20 mg/cc to 1000 mg/cc, from 30 mg/cc to 1000 mg/cc, from 30 mg/cc to 1000 mg/cc, from 30 mg/cc to 900 mg/cc, from 30 mg/cc to 800 mg/cc, or from 30 mg/cc to 700 mg/cc).

The density of 3-D structure can be determined using various methods known in the art (see, e.g., Lowell, S. et al., Characterization of porous solids and powders: surface area, pore size and density, published by Springer, 2004). Exemplary methods include, Brunauer Emmett Teller (BET) method and helium pycnometry (see, e.g., Varadan V. K. et al., Nanoscience and Nanotechnology in Engineering, published by World Scientific, 2010). Briefly, in BET method, dry powders of the testing 3-D structure is placed in a testing chamber to which helium and nitrogen gas are fed, and the change in temperature is recorded and the results are analyzed and extrapolated to calculate the density of the testing sample. In helium pycnometry method, dry powders of the testing 3-D structure are filled with helium, and the helium pressure produced by a variation of volume is studied to provide for the density. The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the 3-D structure is fully extended in a buffer solution.

In certain embodiments, the density of the 3-D structure can be determined using the dry mass of the 3-D structure divided by the total volume of such 3-D structure in an aqueous solution. For example, dry mass of the core particles with and without the 3-D structure can be determined respectively, and the difference between the two would be the total mass of the 3-D structure. Similarly, the volume of a core particle with and without the 3-D structure in an aqueous solution can be determined respectively, and the difference between the two would be the volume of the 3-D structure on the core particle in an aqueous solution.

In certain embodiments, the porous nanostructure can be dispersed as multiple large nanoparticles coated with the 3-D structure in an aqueous solution, in such case, the total volume of the 3-D structure can be calculated as the average volume of the 3-D structure for an individual large nanoparticle multiplied with the number of the large nanoparticles.

For each individual large nanoparticle, the size (e.g., radius) of the particle with 3-D structure can be determined with Dynamic Light Scattering (DLS) techniques, and the size (e.g., radius) of the particle core without the 3-D structure can be determined under Transmission Electron Microscope (TEM), as the 3-D structure is substantially invisible under TEM. Accordingly, the volume of the 3-D structure on an individual large nanoparticle can be obtained by subtracting the volume of the particle without 3-D structure from the volume of the particle with the 3-D structure.

The number of large nanoparticles for a given core mass can be calculated using any suitable methods. For example, an individual large nanoparticle may be composed of a plurality of small nanoparticles which are visible under TEM. In such case, the average size and volume of a small nanoparticle can be determined based on measurements under TEM, and the average mass of a small nanoparticle can be determined by multiplying the known density of the core material with the volume of the small particle. By dividing the core mass with the average mass of a small nanoparticle, the total number of small nanoparticles can be estimated. For an individual large nanoparticle, the average number of small nanoparticles in it can be determined under TEM. Accordingly, the number of large nanoparticles for a given core mass can be estimated by dividing the total number of small nanoparticles with the average number of small nanoparticels in an individual large nanoparticle.

Alternatively, the low density, porous 3-D structure refers to a structure having 40%-99.9% (preferably 50% to 99.9%) of empty space or pores in the structure, where 80% of the pores having size of 1 nm to 500 nm in pore radius.

The porosity of the 3-D structure can be characterized by the Gas/Vapor adsorption method. In this technique, usually nitrogen, at its boiling point, is adsorbed on the solid sample. The amount of gas adsorbed at a particular partial pressure could be used to calculate the specific surface area of the material through the Brunauer, Emmit and Teller (BET) nitrogen adsorption/desorption equation. The pore sizes are calculated by the Kelvin equation or the modified Kelvin equation, the BJH equation (see, e.g., D. Niu et al., *J. Am. chem. Soc.* 132, 15144-15147 (2010)).

The porosity of the 3-D structure can also be characterized by mercury porosimetry (see, e.g., Varadan V. K. et al., supra). Briefly, gas is evacuated from the 3-D structure, and then the structure is immersed in mercury. As mercury is non-wetting at room temperature, an external pressure is applied to gradually force mercury into the sample. By monitoring the incremental volume of mercury intruded for each applied pressure, the pore size can be calculated based on the Washburn equation.

Figure 2:
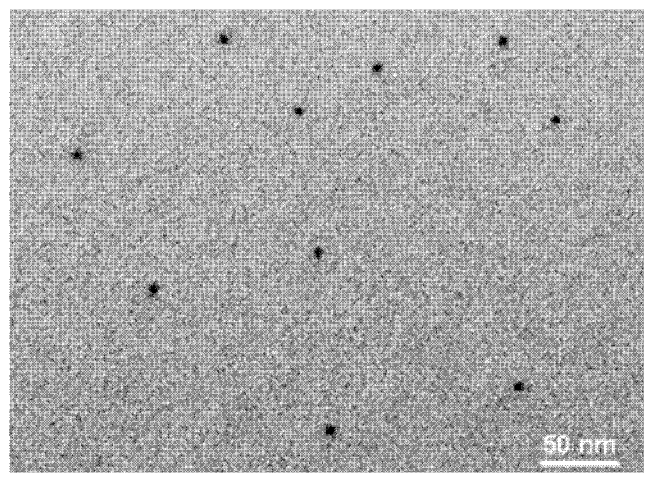
FIG. 2. An exemplary TEM image of silanized quantum dots with nanoparticle core size of ~6 nm and hydrodynamic size ~200 nm. The siliceous coating is not obviously visible from the TEM.
Figure 3:
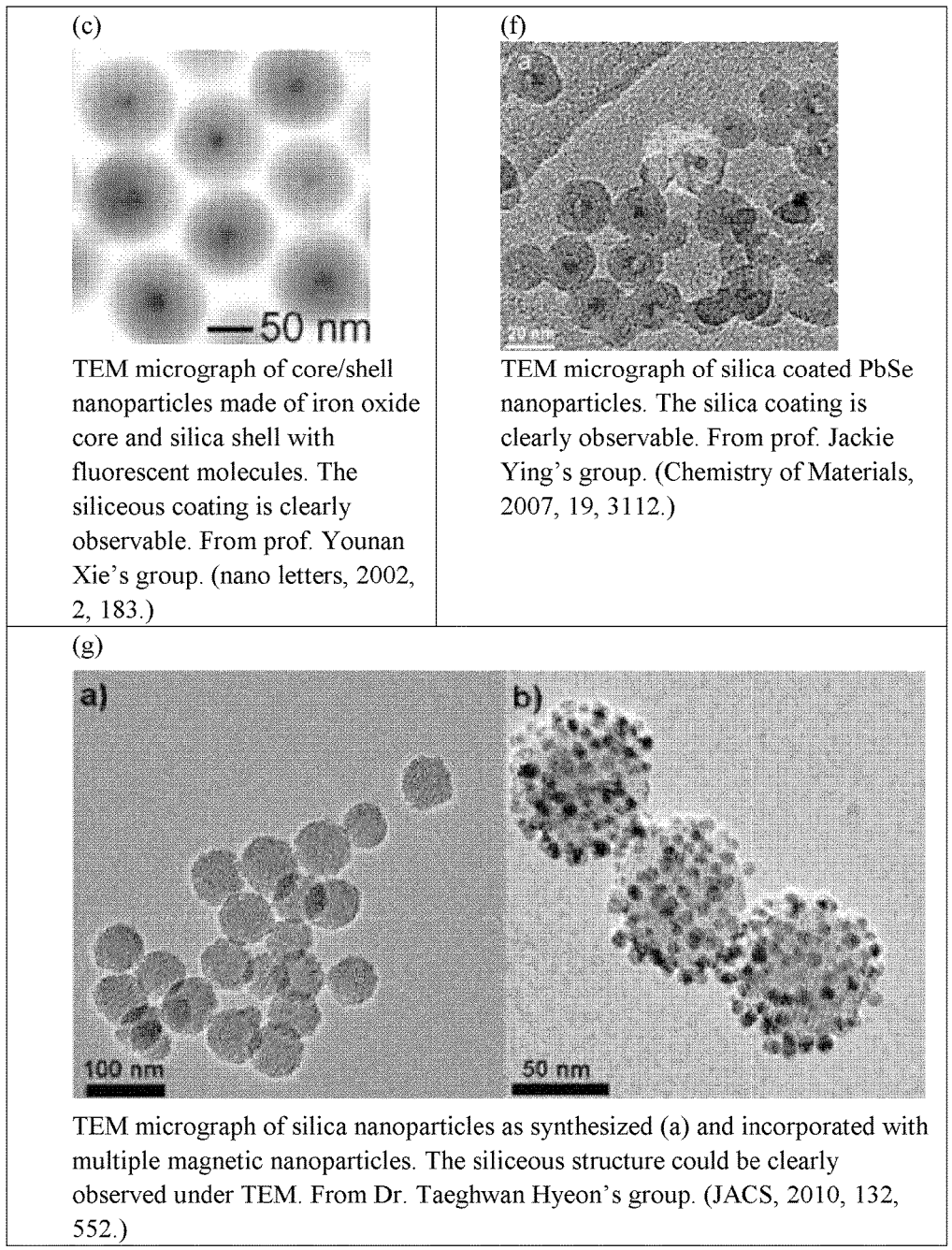
FIG. 3. Exemplary TEM images of coated nanoparticles known in the art, in which the coatings are obviously observable under TEM.

Alternatively, the low density, porous 3-D structure refers to a structure that has a material property, that is, the porous structure (except to the core nanoparticle or core nanoparticles) could not be obviously observed or substantially transparent under transmission electron microscope, for example, even when the feature size of the 3-D structure is in the 10 s or 100 s nanometer range. The term "obviously observed" or "substantially transparent" as used herein means that, the thickness of the 3-D structure can be readily estimated or determined based on the image of the 3-D structure under TEM. The nanostructure (e.g., nanoparticles coated with or embedded in/on a low density porous 3-D structure) can be observed or measured by ways known in the art. For example, the size (e.g., radius) of the nanostructure with the 3-D structure can be measured using DLS methods, and the size (e.g., radius) of the core particle without the 3-D structure can be measured under TEM. In certain embodiments, the thickness of the 3-D structure is measured as 10 s, 100 s nanometer range by DLS, but cannot be readily determined under TEM. For example, when the nanostructures provided herein are observed under Transmission Electron Microscope (TEM), the nanoparticles can be identified, however, the low density porous 3-D structure can not be obviously observed, or is almost transparent (e.g., see FIGS. 1 and 2). This distinguishes the nanostructures provided herein from those reported in the art (see, FIG. 3) that comprise nanoparticles coated with crosslinked and size tunable 3-D structure, including the mesoporous silica nanoparticles or coating (see, e.g., J. Kim, et. al., J. Am. Chem. Soc., 2006, 128, 688-689; J. Kim, et. al., Angew. Chem. Int. Ed., 2008, 47, 8438-8441). This feature also indicates that the low density porous 3-D structure provided herein has a much lower density and/or is highly porous in comparison to other coated nanoparticles known in the art.

Figure 4:
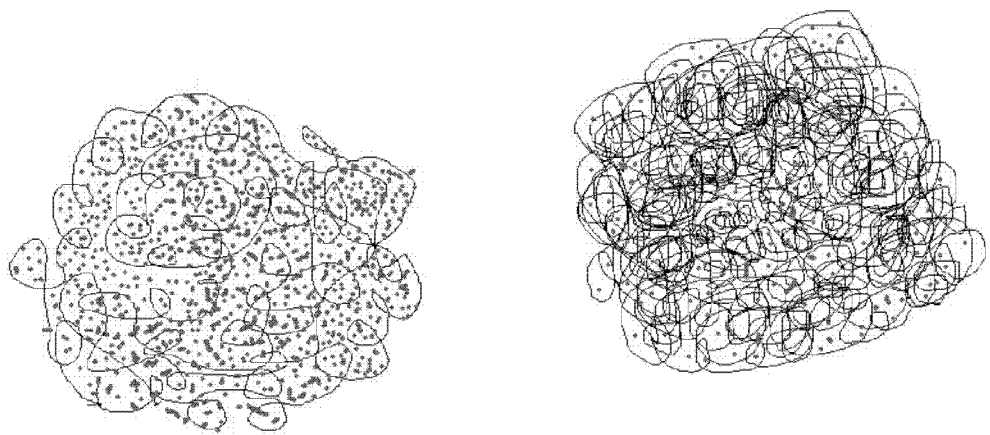
FIG. 4. A schematic comparison of porous nanostructure incorporating a plurality of payloads (dots) with dense nanostructures (black network, right).

The porosity of the 3-D structure can be further evaluated by the capacity to load different molecules (see, e.g., Wang L. et al., *Nano Research* 1, 99-115 (2008)). As the 3-D structure provided herein has a low density, it is envisaged that more payload can be associated with the 3-D structure than with other coated nanoparticles (see, e.g., FIG. 4). For example, when 3-D structure is loaded with organic fluorophores such as Rhodamin, over $10^5$ Rhodamin molecules can be loaded to 3-D structure of one nanoparticle.

In certain embodiments, the low density structure refers to a structure capable of absorbing or carrying a fluorescent payload whose fluorescence intensity is at least 100 fold of that of the free fluorescent molecule (e.g., at least 150 fold, 200 fold, 250 fold, 300 fold, 350 fold, 400 fold, 450 fold, 500 fold, 550 fold or 600 fold). The fluorescence intensity of a loaded nanoparticle can be quantified under the same excitation and emission wave lengths as that of the fluorescent molecules. The fluorescence intensity of the loaded low density structure indicates the payload of the fluorescent molecule, and also indirectly reflects the porosity of the low density structure.

In certain embodiments, the low density, porous 3-D structure is made of silane-containing or silane-like molecules (e.g., silanes, organosilanes, alkoxysilanes, silicates and derivatives thereof).

In certain embodiments, the silane-containing molecule comprises an organosilane, which is also known as silane coupling agent. Organosilane has a general formula of $R_xSiY_{(4-x)}$, wherein R group is an alkyl, aryl or organofunctional group. Y group is a methoxy, ethoxy or acetoxy group. x is 1, 2 or 3. The R group could render a specific function such as to associate the organosilane molecule with the surface of the core nanoparticle or other payloads through covalent or non-covalent interactions. The Y group is hydrolysable and capable of forming a siloxane bond to crosslink with another organosilane molecule. Exemplary R groups include, without limitation, disulphidealkyl, aminoalkyl, mercaptoalkyl, vinylalkyl, epoxyalkyl, and methacrylalkyl, carboxylalkyl groups. The alkyl group in an R group can be methylene, ethylene, propylene, and etc. Exemplary Y groups include, without limitation, alkoxyl such as $OCH_3$, $OC_2H_5$, and $OC_2H_4OCH_3$. For example, the organosilane can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis[3-(triethoxysilyl) propyl]-tetrasulfide, Bis-[3-(triethoxysilyl) propyl]-disulfide, aminopropyltriethoxysilane, N-2-(aminoethyl)-3-amino propyltrimethoxysilane, Vinyltrimethoxysilane, Vinyl-tris (2-methoxyethoxy) silane, 3-methacryloxypropyltrimethoxy silane, 2-(3,4-epoxycyclohexy)-ethyl trimethoxysilane, 3-glycidoxy-propyltriethoxysilane, 3-isocyanatopropyltriethoxysilane, and 3-cyanatopropyltriethoxysilane.

Payloads

In certain embodiments, the nanocomposition may further comprise a payload, which is carried or associated with the nanostructure. The payloads to be carried or associated with the nanostructure include, but are not limited to, a detectable agent, a biological active agent, a drug, a therapeutic agent, a radiological agent, a chemological agent, a small molecule drug, a biological drug (e.g., peptides, proteins, antibodies, antigens, nucleic acids, aptamers, and the like) and combinations thereof, which can be used to image, detect, study, monitor, evaluate, screen, the analyte of interest. Payloads may be physically absorbed into the porous structure or linked to the porous structure through functional groups disclosed herein. Payloads herein also include analyte-capturing members that bind specifically to the analyte of interest.

A detectable agent can be a fluorescent molecule, a chemo-luminescent molecule, a bio-luminescent molecule, a radioisotope, a MRI contrast agent, a CT contrast agent, an enzyme-substrate label, and/or a coloring agent etc. Examples of fluorescent molecules include, without limitation, fluorescent compounds (fluorophores) which can include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa® Fluor 350; Alexa® Fluor 405; Alexa® Fluor 500; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin);

AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (nonratio); DiA (4-Di-16-ASP); Dichlorodihydrofluorescein Diacetate (DCFH); DiD-Lipophilic Tracer; DiD (DiIC18 (5)); DIDS; Dihydrorhodamine 123 (DHR); DiI (DiIC18 (3)); Dinitrophenol; DiO (DiOC18(3)); DiR; DiR (DiIC18 (7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), fluorescent semiconductor nanoparticles, lanthanides or combinations thereof.

Examples of radioisotopes include, $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, $^{32}P$, $^{18}F$, $^{201}Tl$, $^{67}Ga$, $^{137}Cs$ and other radioisotopes.

Examples of enzyme-substrate labels include, luciferases (e.g., firefly luciferase and bacterial luciferase), luciferin, 2,3-dihydrophthalazinedionesm, alate dehydrogenase, urease, peroxidase such as horseradish peroxidase (HRPO), alkaline phosphatase, -galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

In certain embodiment, at least one payload can be associated with the nanostructure. For example, only one group of homogenous payloads are associated with the nanostructure. For another example, the first payload and the second payload are associated with the nanostructure and can be different.

In certain embodiments, the first payload is associated with the nanostructure in one area of the structure and the second payload is associated with the nanostructure in another area of the structure so that the nanostructure can be directional or oriented with respect to the distribution of payloads in the nanostructure. Such site selective modification could be achieved by depositing the nanostructure on a substrate, then partially coating the substrate with a protective polymer layer, such as poly(3-hexyl-thiophene) (P3HT) and poly(methyl methacrylate) that could be dissolved using certain solvents such as chloroform or pyridine after the site selective modification is finished. (Liu H., et. al., nano letters, 2004, vol 4., 2397-2401). A second modification could be achieved after the protective layer is removed and the unmodified nanostructure is exposed and further modified with different payloads. Further, the nanostructure could be deposited on the substrate with bonding through cleavable molecules, for example, photo cleavable molecules such as photocleavable biotin amine reactive labeling reagents (www.ambergen.com), then the nanostructure could be released after site selective modifications. In addition, with cleavable linker molecule bound to the substrate, the nanostructures could be released after the first site selective modification (SSM1). SSM1 could include both functional groups for linking the SSM1 modified area to a substrate in the next site selective modification step and payloads for signal generating, drugs or other functional purposes. The procedure could be repeated for SSM2. By controlling the protective polymer layer thickness, 3rd, 4th or more site selective modification steps could be carried out to render the nanostructures multiple regions of different payloads.

Methods of Use

Another aspect of the present disclosure relates to methods of capturing, enriching, purifying, detecting or measuring analytes at a sub-nanogram level. The methods comprise steps of contacting an analyte-containing sample with a nanocomposition disclosed herein to form a mixture (e.g., in a solution) and allow the binding of an analyte with the nanocomposition mixture (e.g., analyte-nanocomposition conjugate whereas the nanocomposition binds to the analyte via an analyte-capturing member), applying a magnetic field to the mixture, and eluting the analytes from the nanocomposition. The method further comprises the step of washing the mixture prior to elution.

Figure 5:
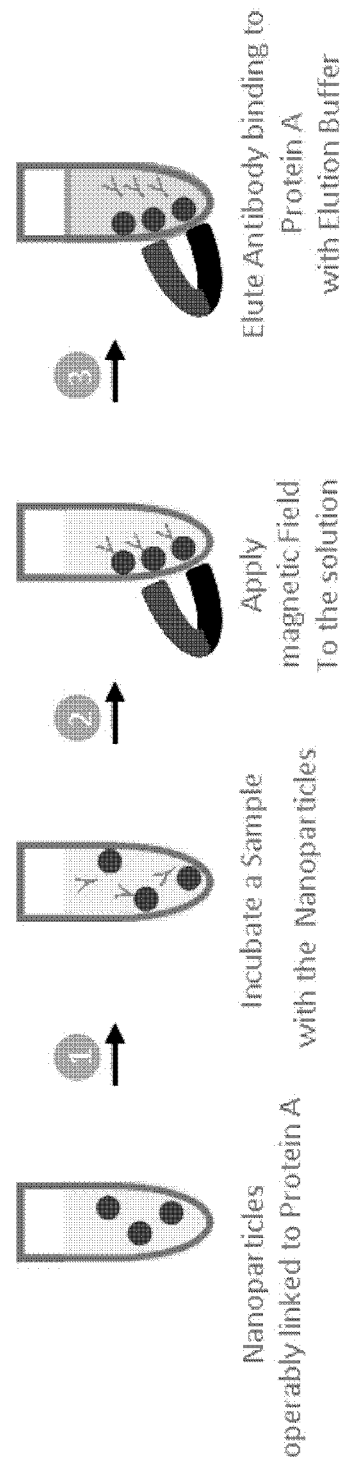
FIG. 5. Illustration of the molecular enrichment and purification process using magnetic nanocomposition disclosed herein.

Referring to FIG. 5, a nanocomposition is obtained by operably linking the nanostructure disclosed herein to Protein A (an analyte-capturing member) and the nanocomposition is incubated with a sample in a solution comprising an antibody for a period of time (e.g. 2 hrs) to allow Protein A to fully capture or bind to the antibody. Then the antibody-bounded nanocomposition is attracted and separated from other elements in the sample by applying a magnetic field to the solution in a container. In the presence of a magnetic field, the sample-containing solution is removed and the antibody-nanostructures are attracted to the magnetic field and left in the container. In a further step, the antibody is separated from Protein A or from the nanocomposition by applying the elution buffer to the container wherein the elution buffer is sufficient to separate the binding of the antibody to Protein A. The magnetic field is applied then to attract nanostructure while the separated, un-bounded antibodies are in the eluate.

In certain embodiments, the method further comprises a step of washing the nanocomposition in the presence of magnetic field after removing the liquid and before eluting. As shown in FIG. 5, for example, after removing the liquid from the mixture solution, the nanocomposition is redispersed in suitable washing liquid and then separated again by applying a magnetic field. The washing step can be carried out repeatedly.

In certain embodiments, the method further comprises a step of analyzing the eluate by detecting the presence of the analyte or quantifying the amount of the analyte at a sub-nanogram level. As shown in FIG. 5, for example, the antibody binding to Protein A is eluted from the nanocomposition with an elution buffer. The eluate is collected and analyzed with methods known in the art.

Another aspect of the present disclosure relates to a method of selecting or capturing an analyte (e.g., a cell) comprising the steps of determining and applying a ratio of nanocompositions per said analyte and mixing the nanocompositions with said analyte based on the ratio. In certain embodiments, an increase in the ratio of nanocomposition to the analyte can enhance the chance and/or amount of the analyte captured from the sample. Such methods can also be useful when a trace amount of analyte is to be separated or captured, for example, for identification of circulating tumor cells, circulating DNAs in whole blood sample, or certain marker cells expressing an interested biomarker (e.g. a disease cell surface marker, and a stem cell marker, etc.). People in the art can test the recovery rate of the analyte using different ratios of the nanocompositions to the analyte, while fixing the amount of the analyte.

Another aspect of the present disclosure relates to a method of evaluating the bounded nanocompositions per analyte and selecting the analyte with a certain properties that allow them to bind to a desired number of nanocompositions to carry enough magnetic moment to respond to a magnetic pull down. For magnetic nanoparticles that need a certain number of nanoparticles per cell, for example, 10 or 20 nanoparticles per cell to allow the cells to be magnetically pulled down, the analyte bounded with more magnetic nanocompositions more than the threshold of the number of nanoparticles per analyte will be pulled down and magnetically captured when a magnetic field is applied, the analyte bounded with less number of magnetic nanoparticles will not be magnetically pulled down. Such methods are useful for selecting analytes (i.e. cells) having a desired number of markers, for example, selecting hybridoma cells producing a high level of antibodies, or selecting a cell expressing a high level of certain markers. For example, a cell population with different expression level of a certain marker is captured with the nanocomposition when the number of surface marker larger than a certain number. The number of surface marker on the cell surface that allow magnetic capture could be determined by a specific disease indication, for example, cancer vs. normal cells, then the ratio of magnetic nanoparticles vs. the total cell number could be adjusted to allow that specific disease cell portion with a certain level of surface marker to be magnetically pulled down.

Another aspect of the present disclosure relates to methods of determining whether a test agent in a sample specifically binds to an analyte and/or determining the nature of the test agent, comprising the steps of: a) contacting the sample containing an analyte and possibly the agent to be determined with a nanocomposition in a mixture solution and allowing the binding of the agent with the analyte which binds to the nanocomposition, b) applying a magnetic field to the mixture solution, and c) evaluating the presence, the nature, and/or the amount of the agent binding to the analyte.

In certain embodiments, the method further comprises a step of removing liquid from the mixture solution in the presence of the magnetic field.

In certain embodiments, the method further comprises a step of washing the nanocomposition in the presence of magnetic filed after removing the liquid and before eluting.

In certain embodiments, the method further comprises a step of eluting the agent and the analyte from the nanocomposition, and analyzing the presence, nature and/or quantity of the agent. The analyte and the test agent can be eluted separately under different conditions. The method may further comprise recovering the test agent from the eluate.

Figure 6:
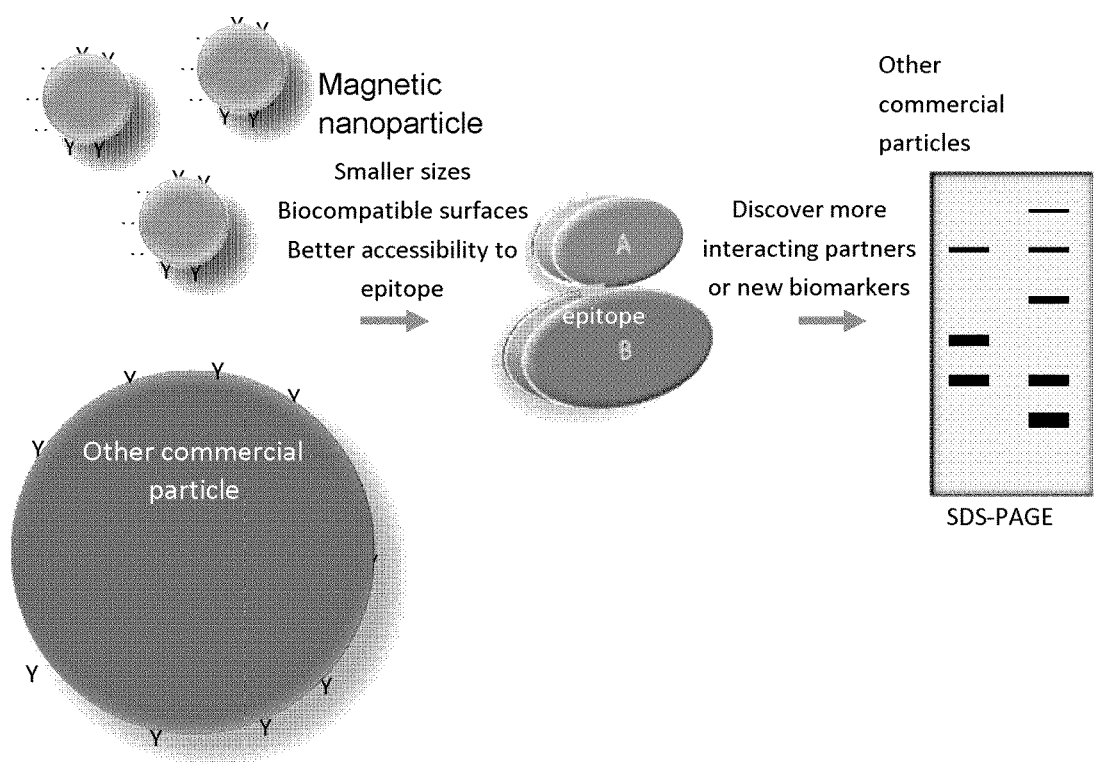
FIG. 6. Illustration of the discovery of novel molecules that bind to the analyte—which binds to nanocomposition disclosed herein.

In certain embodiments, the method is particularly useful for detecting an agent or another protein or biological analyte that binds to a know analyte, in particular, in protein-protein interaction. Other agents that bind to the known analyte can be detected using the method herein and analyzed method well known in the art (e.g., mass spectrum, SDS gel, Western blot, ELISA, or antibodies-based methods) (see FIG. 6).

Methods for Preparing the Composition

Another aspect of the present disclosure relates to methods of forming a nanocomposition comprising a nanostructure operably linked to an analyte-capturing member.

In certain embodiments, the analyte-capturing members may be mixed with a readily formed nanostructure, e.g., in solution, dispersion, suspension, emulsion etc, to allow incorporation of the analyte-capturing members to the porous compartment of the nanostructure, or to allow conjugation of the analyte-binding members to the functional groups on the nanostructure.

In certain embodiments, the analyte-binding members may be introduced during or after the formation of the nanostructures. For example, when the nanostructure is formed through silanization process, the analyte-binding members can be introduced to the silanization system, so as to allow the incorporation of the analyte-binding member into the nanostructure during the silanization process. For another example, for a nanostructure having a surface reactive group (such as streptavidin), the analyte-binding member comprises a binding partner to the reactive group (such as biotin) can be mixed with the nanostructure under conditions which facilitate the binding.

Methods for Preparing the Nanostructure

Another aspect of the present disclosure relates to methods of forming a nanostructure comprising at least one core nanoparticle with a coating. For example, the nanostructure is formed by coating or surrounding one or more core nanoparticle with a coating material such that the particle(s) is or are embedded in the coating material. For another example, the coating material is formed by crosslinking a precursor in the presence of a core nanoparticle, so that the nanoparticle is embedded in the crosslinked coating material.

In certain embodiments, the method further comprises introducing one or more functional groups within or on the surface of the nanostructure. The functional groups may be introduced during the formation of the coating material. For example, during the cross-linking process, precursors containing such functional groups can be added, in particular, during the ending stage of the cross-linking process. The functional groups may also be introduced after the formation of the nanostructure, for example, by introducing functional groups to the surface of the nanostructure by chemical modification. In certain embodiments, the functional groups are inherent in the nanostructure or in the coating material.

The functional groups serve as linkage between the nanostructure and the analyte capturing member. Examples of the functional groups include, but are not limited to amino, mercapto, carboxyl, phosphonate, biotin, streptavidin, avidin, hydroxyl, alkyl or other hydrophobic molecules, polyethylene glycol or other hydrophilic molecules, and photo cleavable, thermo cleavable or pH responsive linkers.

In certain embodiments, the method further comprises purifying the obtained nanostructure product. The purification may include use of dialysis, tangential flow filtration, diafiltration, or combinations thereof.

Methods for Preparing the Nanostructure Having a Low-Density Porous 3-D Structure Another aspect of the present disclosure relates to methods of forming a nanostructure comprising at least one core nanoparticle with low-density, porous 3-D structure. For example, the nanostructure is formed by coating or surrounding one or more core nanoparticle with low density, porous 3-D structure such that the particle(s) is or are embedded in the 3-D structure.

The low-density, porous 3-D structure is formed by the depositing, or covering of the surface of the core nanoparticle through the assembly or cross-linking of silane-containing or silane-like molecules. The low density porous 3-D structure can be prepared by a silanization process on the surface of the core nanoparticles. Silanization process includes, for example, the steps of crosslinking silicon-containing or silane-like molecules (e.g., alkoxysilanes such as amino-propyl-trimethoxysilane, mercapto-propyl-trimethoxysilane, or sodium silicate) under acidic or basic conditions.

In certain embodiments, an acidic or a basic catalyst is used in the crosslinking. Exemplary acid catalyst include, without limitation, a protonic acid catalyst (e.g., nitric acid, acetic acid and sulphonic acids) and Lewis acid catalyst (e.g., boron trifluoride, boron trifluoride monoethylamine complex, boron trifluoride methanol complex, $FeCl_3$, $AlCl_3$, $ZnCl_2$, and $ZnBr_2$). Exemplary basic catalysts include, an amine or a quaternary ammonium compound such as tetramethyl ammonium hydroxide and ammonia hydroxide.

The silanization process may include one or more stages, for example, a priming stage in which the 3-D structure starts to form, a growth stage in which a layer of siliceous structure is readily formed on the core nanoparticle and more are to be formed, and/or an ending stage in which the 3-D structure is about to be completed (e.g., the outer surface of the 3-D structure is about to be formed). During the silanization process, one or more silane-containing molecules can be added at different stages of the process. For example, in the priming stage, organosilanes such as amino-propyl trimethoxyl silane or mercaptopropyl trimethoxyl silane can be added to initiate the silanization on the core nanoparticle surface. For another example, silane molecules having fewer alkoxy groups (e.g., only 2 alkoxy groups) can be added to the reaction at the growth stage of silanization. For another example, at the ending stage of silanization, organo silane molecules with one or a variety of different functional groups may be added. These functional groups can be amino, carboxyl, mercapto, or phosphonate group, which can be further conjugated with other molecules, e.g., hydrophilic agent, a biologically active agent, a detectable label, an optical responsive group, electronic responsive group, magnetic responsive group, enzymatic responsive group or pH responsive group, or a binding partner, so as to allow further modification of the 3-D structure in terms of stability, solubility, biological compatibility, capability of being further conjugation or derivation, or affinity to payload. Alternatively, the functional groups can also be a group readily conjugated with other molecules (e.g., a group conjugated with biologically active agent, a thermal responsive molecule, an optical responsive molecule, an electronic responsive molecule, a magnetic responsive molecule, a pH responsive molecule, an enzymatic responsive molecule, a detectable label, or a binding partner such as biotin or avidin).

To control the formation of low density siliceous structure, the preparation further includes density reducing procedures such as introducing air bubbles in the reaction or formation, increasing reaction temperature, microwaving, sonicating, vertexing, labquakering, and/or adjusting the chemical composition of the reaction to adjust the degree of the crosslinking of the silane molecules. Without being bound to theory, it is believed that these procedures can help make the reaction medium homogeneous, well dispersed and promote the formation of low density porous 3-D structure with increased voids or porosity.

In certain embodiments, the density reducing procedure comprises sonicating the reaction or formation mixture. The conditions of the sonicating procedure (e.g., duration) in the silanization process can be properly selected to produce a desired porosity in the resulting low density porous 3-D structure. For example, the sonicating can be applied throughout a certain stage of the silanization process. The duration of sonicating in a silanization stage may last for, e.g., at least 1 hour, 1.5 hours, 2 hours, 2.5 hours, 3 hours, 3.5 hours, 4 hours. In certain embodiments, sonicating is applied in each stage of the silanization process.

In certain embodiments, the density reducing procedures comprise introducing at least one alcohol to the reaction. In certain embodiments, the alcohol has at least 3 (e.g., at least 4, at least 5 or at least 6) carbon atoms. For example, the alcohol may have 3, 4, 5, 6, 7, 8, 9, 10, 11, 12 or more carbon atoms. In certain embodiments, the alcohol can be monohydric alcohols, or polyhydric alcohols. Illustrative examples of monohydric alcohols include, propanol, butanol, pentanol, hexyl alcohol, etc. Illustrative examples of polyhydric alcohols include, propylene glycol, glycerol, threitol, xylitol, etc. In certain embodiments, the alcohol can have a saturated carbon chain or an unsaturated carbon chain. An alcohol having a saturated carbon chain can be represented as $C_nH_{(2n+2)}O$ in chemical formula. In certain embodiments, n is no less than 3, or no less than 4, or no less than 5 (e.g., n=3, 4, 5, 6, 7, 8, 9, 10, 11, 12 or more). Alcohol with an unsaturated carbon chain has a double or a triple bond between two carbon atoms. In certain embodiments, the alcohol can be a cyclic alcohol, for example, cyclohexanol, inositol, or menthol.

In certain embodiments, the alcohol can have a straight carbon chain (e.g., n-propyl alcohol, n-butyl alcohol, n-pentyl alcohol, n-hexyl alcohol, etc) or a branched carbon chain (e.g., isopropyl alcohol, isobutyl alcohol, tert-butyl alcohol, etc). In certain embodiments, the alcohol is present in a volume fraction of about 30% to about 70% (e.g., about 30% to about 70%, about 30% to about 60%, about 30% to about 55%, about 40% to about 70%, about 45% to about 70%, about 40% to about 60%). In certain embodiments, the alcohol is present in volume fraction of around 50% (e.g., around 45%, around 46%, around 47%, around 48%, around 49%, around 50%, around 51%, around 52%, around 53%, around 54%, around 55%, around 56%, around 57%, around 58%, around 59%, or around 60%).

In certain embodiments, the density reducing procedure comprises introducing air bubbles to the reaction. In certain embodiments, the air bubbles can be in constant presence during the reaction process. The air bubbles can be introduced to the reaction through any suitable methods, for example, by blowing bubbles to the reaction, or by introducing a gas-producing agent to the reaction mixture.

Other experimental conditions can also be optimized to provide for formation of a desired low density porous 3-D structure. Such experimental conditions include, for example, the concentration of the core nanoparticles, the concentration of the catalyst, the ratio of the concentration of the catalyst to the core nanoparticle, the temperature at which the low density siliceous structure is formed, or the molecular structure of the organosilanes.

The thickness of the low density porous 3-D structure, which directly correlates to the size of the nanostructure, could be controlled (e.g., from 1 nm to 1000 nm) by, for example, modifying the quantity of the silane-containing molecules (e.g., trialkoxysilane or sodium silicate), the reaction time, and time lapse between reaction steps and such kind of reaction parameters.

The thickness of the 3-D structure can be about 1 to 5 nm thick. In certain embodiments, the thickness can be about 1 to 10 nm thick. In certain embodiments, the thickness can be about 1 to 20 nm thick. In certain embodiments, the thickness can be about 1 to 30 nm thick. In certain embodiments, the thickness can be about 1 to 40 nm thick. In certain embodiments, the thickness can be about 1 to 50 nm thick. In certain embodiments, the thickness can be about 1 to 60 nm thick. In certain embodiments, the thickness can be about 1 to 100 nm thick. In certain embodiments, the thickness can be about 1 to 500 nm thick. In certain embodiments, the thickness can be about 1 to 1000 nm thick.

After the low-density, porous 3-D structure is formed on the surface of the core nanoparticle, the core nanoparticle is embedded in the 3-D structure. The resulting nanostructure can have a thickness (e.g., the longest dimension of the nanostructure or a diameter if the structure is a sphere) of about 1 to 1000 nm, 1 to 100 nm, or 1 to 10 nm. In another embodiment, the nanostructure can have a diameter of about 1 to 30 nm. In another embodiment, the nanostructure can have a diameter of about 500 nm. In another embodiment, the nanostructure can have a diameter of about 100 nm. In another embodiment, the nanostructure can have a diameter of about 50 nm. In another embodiment, the nanostructure can have a diameter of about 30 nm. In another embodiment, the nanostructure can have a diameter of about 10 nm.

Products by Process

Another aspect of the present disclosure relates to nanocomposition prepared by any of the methods provided herein. The nanocomposition prepared herein may be operably linked with one or more analyte-capturing members, using methods described herein and/or conventional methods known in the art. The nanocomposition prepared in the present disclosure can be further characterized for the 3-D structure, such as density, porosity, surface areas, thickness etc. of the 3-D structure. Optionally, the analyte-capturing members may be characterized as well, such as the amount of the analyte-capturing member or the detectable signal of the analyte-capturing member.

EXAMPLES

Example 1. Preparation of Nanoparticles of Gold and Semiconductor Quantum Dots with the Low Density Siliceous Structure The low density siliceous structure is a versatile and flexible platform for making biocompatible nanoparticles. For example, to incorporate gold nanoparticles into the siliceous structure, Au nanoparticles synthesized in either water solution or organic solutions could be utilized. Briefly, Au was precipitated out at the sample vial bottom after centrifuge at 13 k rpm for 15 min, then silane molecules such as aminopropyltrimethoxysilane and TMAOH was added. The reaction solvent was adjusted using a higher number alcohol, such as butanol or proponol. Then the sample was sonicated for a few hours with constant blowing of air bubbles, afterwards, PEG-silane, mercaptopropyltrimethoxysilane and aminopropyltrimethoxysilane were added, the sample was sonicated for additional 2-3 hours. Afterwards, mixture of chlorotrimethylsilane, methanol, and TMAOH or other silane molecules that only have one alkoxyl group connecting with the silicon atom were added to react with surface siloxyl groups presented on the surface of the already grown siliceous structure. After additional sonicating and aging, stable nanoparticles with the highly porous siliceous structure were collected and stored within physiological buffer solutions through centrifugal filtering, centrifugation, dialysis or any other solution exchange methods. The resulting Au nanostructure was observed under TEM, and an exemplary TEM image was shown in FIG. 1. The nanoparticle core size was about 20 nm and hydrodynamic size was about 60 nm. The siliceous coating was not obvious from the TEM.

Example 2. Preparation of Nanoparticles of Semiconductor Quantum Dots with the Low Density Siliceous Structure As another example, semiconductor quantum dots in the form of individual nanocrystal or nanocrystal clusters could also be incorporated within the highly porous/low density siliceous structure. For example, CdSe/ZnS nanoparticles in organic solvents such as chloroform, Toluene, or Hexane could be precipitated out by adding methanol and then through centrifugation. The nanocrystal pellet was then re-dispersed in aminopropyltrimethoxysilane or mercaptopropyltrimethoxysilane. Afterwards, tetramethyl ammonium hydroxide was added. Then the reaction solvent was adjusted using a higher number alcohol, such as butanol or proponol. After sonicating the sample for 1-4 hours and blowing air bubbles, small amount of aminopropyltrimethoxysilane, mercaptopropyltrimethoxysilane, polyethyleneoxidesilane and water was subsequently added, and the sample then underwent sonication for another 1 to 4 hours. Then, mixture of chlorotrimethylsilane, methanol, and TMAOH or other silane molecules that only have one alkoxyl group connecting with the silicon atom were added. This sample was then sonicated for another 1-4 hours, followed by overnight aging under mild shaking or vibration. The resulting nanoparticles with low density/highly porous siliceous structure were transferred into physiological buffer solutions by centrifugal filtering, centrifugation, dialysis or any other solution exchange methods. The resulting CdSe/ZnS nanostructure was observed under TEM, and an exemplary TEM image was shown in FIG. 2. The nanoparticle core size was about 10 nm and hydrodynamic size was about 200 nm. The siliceous coating was not obvious from the TEM.

Figure 7:
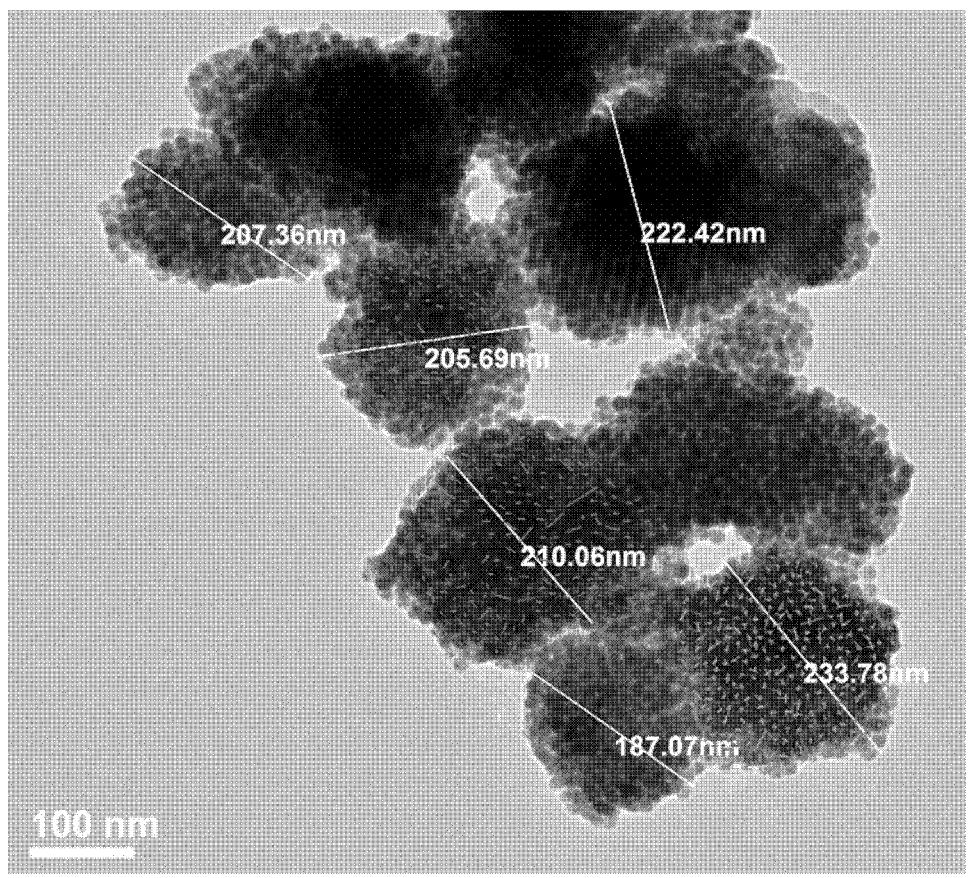
FIG. 7. An exemplary TEM image of porous nanostructure, in which the diameters of the large core nanoparticles are shown.

Example 3. Preparation and Characterization of Low Density Magnetic Particles Preparation of the Magnetic Porous Nanostructure:

Magnetic particles formed by clustering multiple small particles and then being coated were prepared. The clustering happened with the addition of a worse solvent for generating dispersed nanoparticles, such as butanol or isopropanol, followed by the addition of the silanization reagents to form the porous nanostructure under constant blowing of air bubbles. The magnetic porous nanostructure as prepared was observed under TEM (FIG. 7). As shown in FIG. 7, each large core nanoparticle comprised a cluster of small nanoparticles, and the coating was substantially invisible under TEM.

Characterization of Density of the Coating:

To calculate the density of the coating, both the dry mass and the volume of the coating were characterized.

Since the magnetic particles had high magnetic response that they could be directly captured using a magnet. This allowed generation of dry particles to measure the mass of the material. The dry mass of particles before and after coating was quantified as follows. 200 ul of the coated particle solution was pipetted out into a centrifugal vial whose mass was pre-measured. Coated magnetic nanoparticles were captured to the side of the vial wall, and the supernatant was removed. The captured particles were washed with water. At the end, the particles absorbed to the side wall were left to dry in the open vial under a fume hood. The mass of the vial with the dry coated particles were measured. The dry coated particle mass was calculated by subtraction of the mass of the vial from the mass of the vial with the dry coated particles inside. To measure the mass of the particles before coating, uncoated particles corresponding to the same amount of the magnetic material as in the coated nanoparticles, assuming an 80% coating processing yield, was captured to the side of the vial, and dried. The dry mass of the particles before coating was measured by subtraction of the mass of the vial from the mass of the vial with the dry uncoated particles inside. The mass of the coating was equal to the mass of the dry coated particles minus the dry mass of particles before coating.

TABLE 1

| | |
|---|---|
| Average Core mass (n = 3) | 0.67 mg |
| Average Coating mass (n = 3) | 0.06 mg |

The total volume of the coating was calculated using the number of large particles in the above mass multiplied by the volume of the coating of each individual large nanoparticles. The particles were suspended in an aqueous solution, and the volume of the coating of each large particle was calculated as $4/3 \times \pi (R^3_{with\ coating} - R^3_{core})$, in which the $R_{with\ coating}$ of an individual large nanoparticle was measured using dynamic light scattering (DLS) technique, and the $R_{core}$ of the large core particle was directly imaged and measured using TEM (see FIG. 7).

TABLE 2

| | |
|---|---|
| Average size of large core nanoparticles under TEM | 210 nm |
| Average size of coated large nanoparticles under DLS | 217-357 nm |
| Average coating volume of an coated large nanoparticle | $4/3 \times \pi\ (110^3 - 105^3)$ nm$^3$ |

The number of large particles in the mass was calculated by dividing the total number of small nanoparticles by the number of small nanoparticles in each large nanoparticle. The total number of small nanoparticles was estimated by dividing the mass of total magnetic material by the mass of an individual small nanoparticle (i.e. calculated using the size and density of the small nanoparticle). The number of small nanoparticles in each individual large particle was counted from the TEM micrograph. Hence, the total volume of the coating can be calculated as the volume of coating of a large nanoparticle multiplied by the total number of the large nanoparticles.

TABLE 3

| | |
|---|---|
| Core mass | 0.67 mg |
| Density of core | 5.2 kg/m$^3$ |
| Small nanoparticle size | 16 nm |
| Small nanoparticle Volume | $2.1 \times 10^{-24}$ m$^3$ |
| Mass of each small nanoparticle | $1.1 \times 10^{-17}$ mg |
| Number of small particles in the core | $6.1 \times 10^{16}$ |
| Average number of small particle per large particle | 236 |
| Number of large particles in the core | $2.6 \times 10^{14}$ |
| Total volume of the coating | $4/3 \times \pi$ $(110^3 - 105^3)$ nm$^3 \times$ $2.6 \times 10^{14}$ = $0.1875 \times 10^{-6}$ m$^3$. |

The density of the coating was calculated using the mass of the coating divided by the total volume of the coating, i.e., 0.06 mg/0.1875×10$^{-6}$ m$^3$=0.32 mg/cm$^3$.

The density of the low density siliceous structure prepared herein is only 0.32 mg/cm$^3$, which is significantly lower than the density of some reported silica coatings, for example, those reported in Vincent et al (Vincent, A. et al, J. Phys. Chem. C 2007, 111, 8291-8298), that have a density of 1-2 g/cc and are 10$^4$ denser than the siliceous structure provided herein.

Characterization of Porosity Using BET Method:

Large magnetic nanoparticles after coating were captured to the side of the vial and dried. 2 samples of 65 mg (sample 1) and 45 mg (sample 2) dry mass were prepared for the BET measurement.

Surface pore sizes were measured using BET method for the dry mass of the coated nanoparticles. The results are shown in the below Tables.

TABLE 4

Characterization for Sample 1

| | |
|---|---|
| Surface Area | 14.166 m$^2$/g |
| Total pore volume for pores smaller than 677.5 Å (Radius) at P/P$_0$ = 0.98562 | $7.562 \times 10^{-2}$ cc/g |

TABLE 5

Characterization for Sample 2

| | |
|---|---|
| Surface Area | 6.380 m$^2$/g |
| Total pore volume for pores smaller than 683.3 Å (Radius) at P/Po = 0.98575 | $7.099 \times 10^{-2}$ cc/g |

The surface area and the pore volume of the porous nanostructure were measured with dry mass of the porous nanostructure. If measured with a porous nanostructure sample suspended in an aqueous solution, the pore volume and the surface area are expected to be much higher than the measurements with the dry mass, as the density of the coating has been shown to be at least 10$^4$ lower than those reported in the art.

The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the porous nanostructure is fully extended in a buffer solution.

Example 4. Separation of an Antibody from a Sample

The magnetic porous nanostructures as prepared in Example 3 were operably linked to Protein A. Briefly, protein A was firstly activated with a crosslinker such as SMCC that could then be conjugated to nanoparticle surface. In general, the nanoparticle surfaces were saturated with protein A molecules for maximal binding. The binding capacity of the magnetic nanoparticle-protein A conjugates could be characterized. One method for such characterization involves mixing different quantities of antibodies to the beads, followed by measuring the amount of un-bound antibodies in the flow through with ELISA, then the quantity of bound antibody to beads could be calculated using the total quantity of antibody introduced minus the quantity of antibody in the flow through. A saturation binding quantity of antibody could be derived from the plateau of the curve. The binding capacity of antibodies of the magnetic nanoparticle-protein A samples range from 50 ug/mg beads to 300 ug/mg beads based on the properties of antibody and the measurement methods.

The protein A nanocomposition was washed twice in PBS-T by applying a magnetic field. The nanocomposition was collected and re-dispersed in 90 µl of PBS-T, to which 10 µl of input antibody solution was further added ("Input"), containing 100 ng (Sample #2), 1000 ng (Sample #3) or 0.1 ng (Sample #4) antibody. A nanocomposition lacking protein A was used as a control (Sample #1), and was dispersed in 90 µl of PBS-T and was added with 10 µl of antibody solution containing 100 ng antibody. The mixture of nanocomposition and the antibody was mixed well and incubated with rotating at room temperature for 2 hours. Afterwards, a magnet was used to separate the magnetic nanocomposition from the solution, and the flowthrough ("FT") was collected. Afterwards, the antibody captured by the magnetic nanocomposition was eluted with 90 µl of IgG Elution Buffer (21009) for 1 min. 10 µl of 1M Tris (pH=8.0) was added in to neutralize the solution and the final mixture was collected as elute ("Elute").

Figure 8:
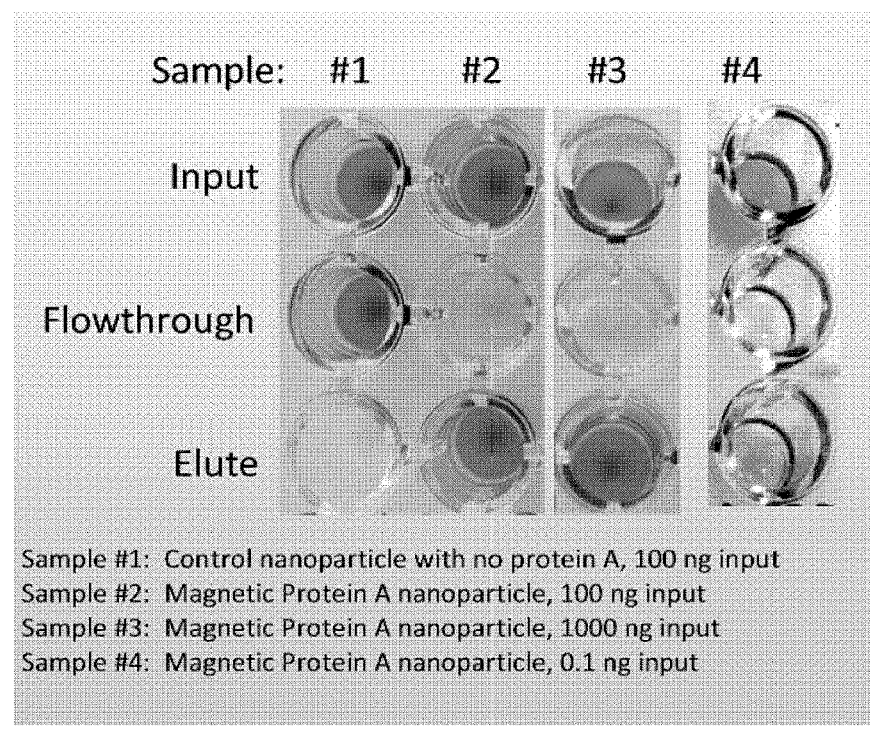
FIG. 8. Magnetic nanostructure-Protein A conjugates show high binding specificity and sensitivity. 0.02 ng of antibodies binding to Protein A can be detected.
Figure 8:
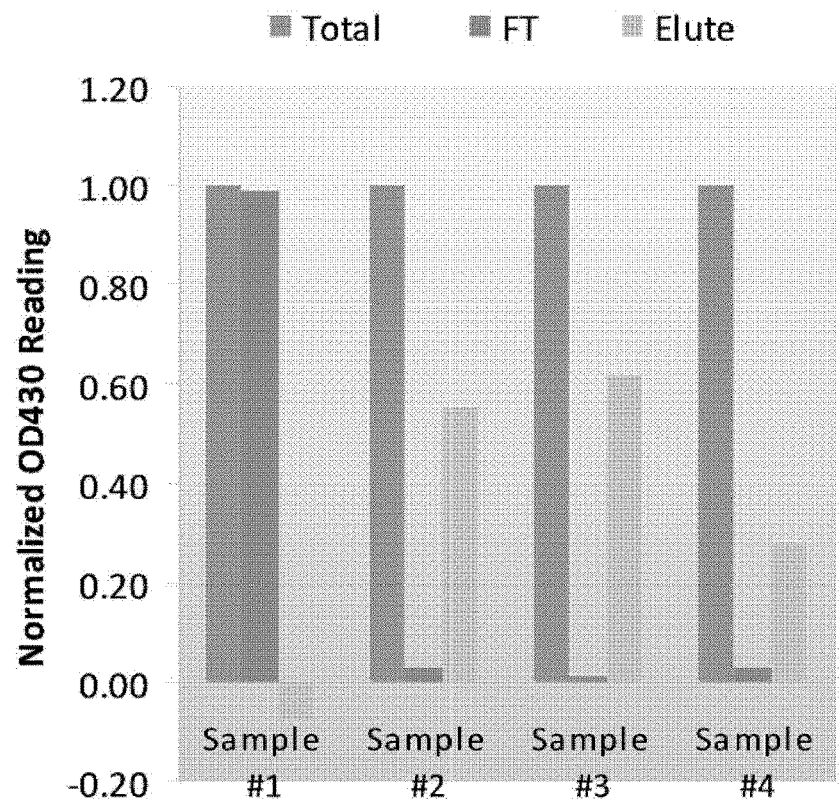

Next, the quantities of antibodies in the input, flowthrough, and elute solutions were quantified with ELISA. The ELISA plate was blocked with 50 ul 1% BSA for 1 hour and washed with PBS-T three times. The samples corresponding to Input, FT, and Elute were diluted 10-fold to 1 ng/µl. When the original quantity of antibody was less than 1 ng/µl, no dilution was performed. 5 µl of each sample and 45 µl of PBS were mixed and every mixture was incubated on an ELISA plate for 1 hour. After washing with PBS-T for three times, the ELISA plate was incubated with 50 µl of HRP (1:50 dilution) at room temperature for 1 hour. Then the ELISA plate was washed with PBS-T for four times and 40 µl of TMB substrate was added. After 6 mins, the pictures of the ELISA plate were taken (see FIG. 8, upper image) and the OD430 was recorded and normalized to the input amount of the antibody. The test result was shown in FIG. 8, lower image. Compared with the negative control (i.e. sample 1# with no Protein A), all the nanocompositions with protein A successfully separated the antibody from the sample, even when the antibody was at a concentration of 0.1 ng.

Figure 9:
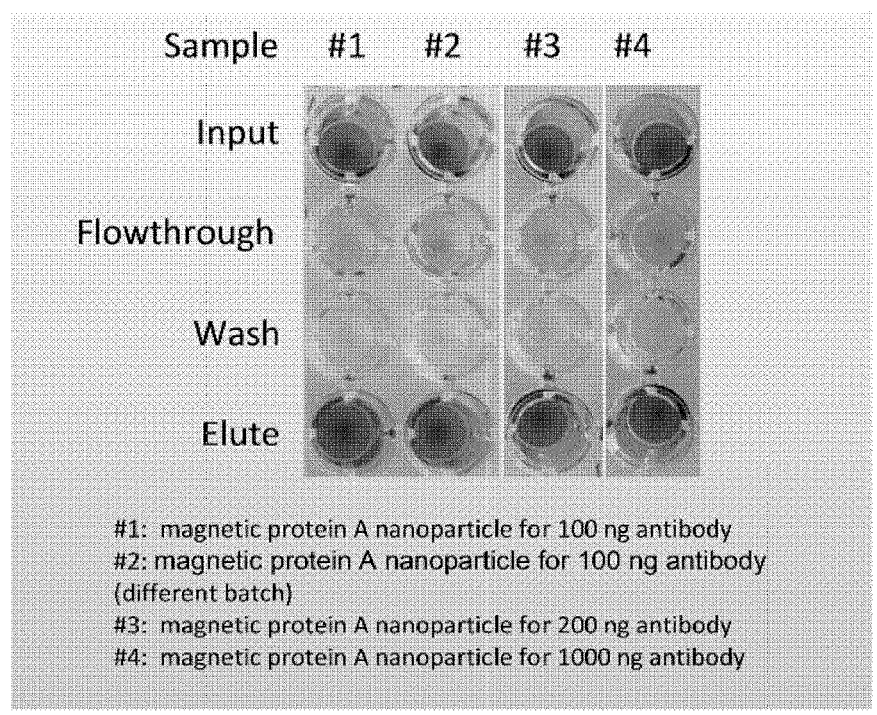
FIG. 9. Magnetic nanostructure-Protein A conjugates show high recovery rates for protein (e.g., antibodies) binding to Protein A.
Figure 9:
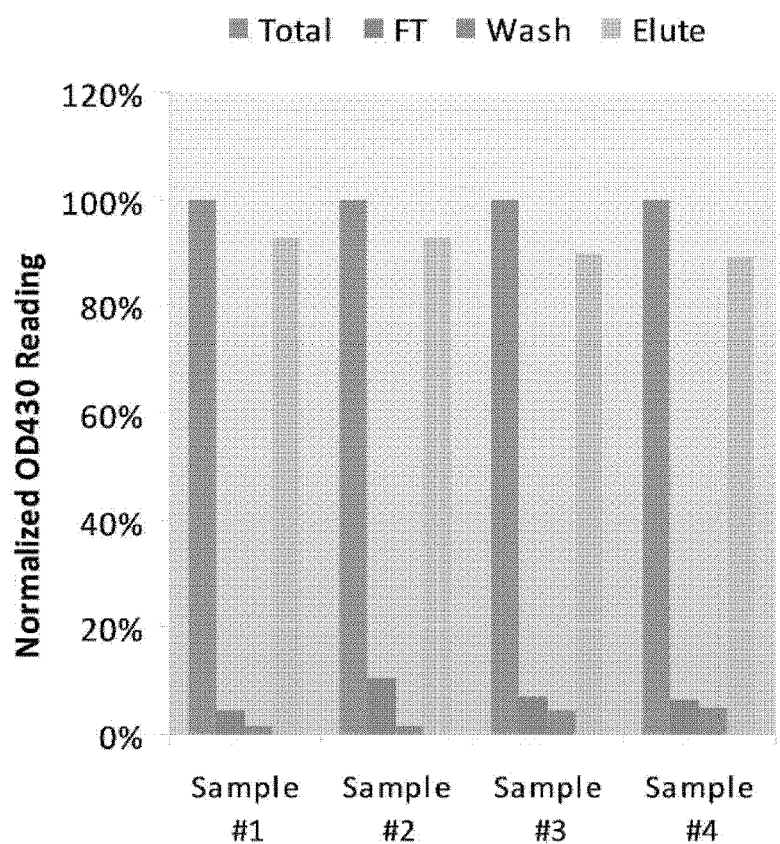

In another experiment, the protein A nanocomposition was used to separate an antibody. The nanocompositions were purified, re-dispersed, and incubated with the antibody, using the same procedure as described above. A magnet was used to separate the magnetic nanocomposition from the solution, and the flow through was collected. The nanocomposition was washed with 100 µl of PBS-C once, and the wash was collected ("Wash"). The antibody captured by the nanocomposition was eluted with the elution buffer, and the eluate was collected as described above. As shown in FIG. 9, the antibody samples, although in different concentrations, were successfully separated with a recovery rate of above 90%. As compared with FIG. 8, the increase in the nanoparticle amount in this experiment resulted in significant increase in recovery rate of the antibody. This indicated that, when separating an analyte in low amount, increasing the amount of nanoparticles can increase the recovery rate.

Figure 10:
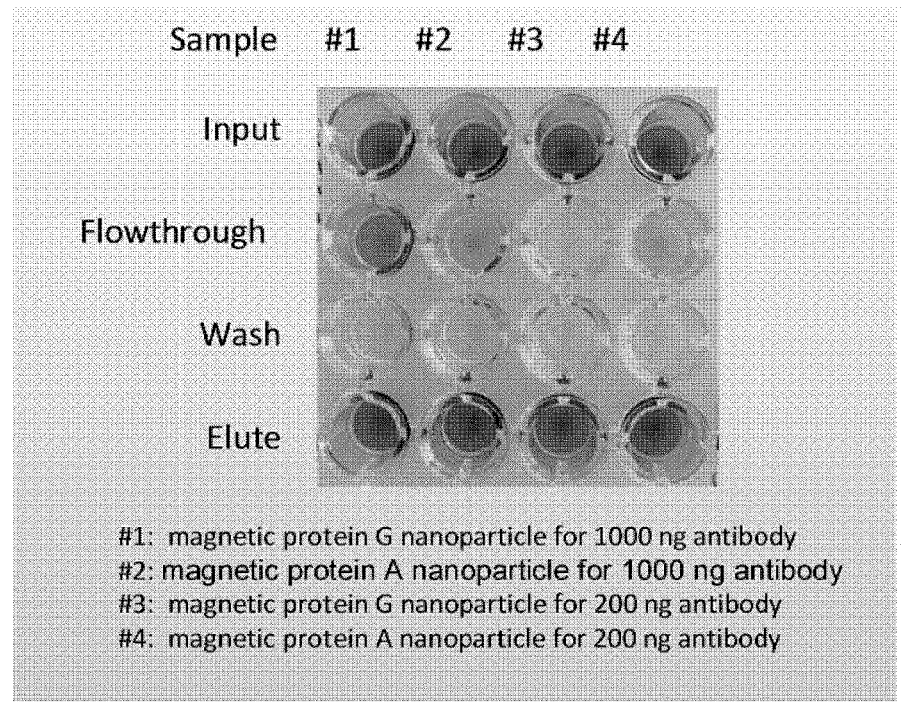
FIG. 10. Both magnetic nanostructure-Protein G (PG) and magnetic nanoparticle-protein A (PA) conjugates show high recovery rates for protein (e.g., antibodies) binding to Protein A or G).
Figure 10:
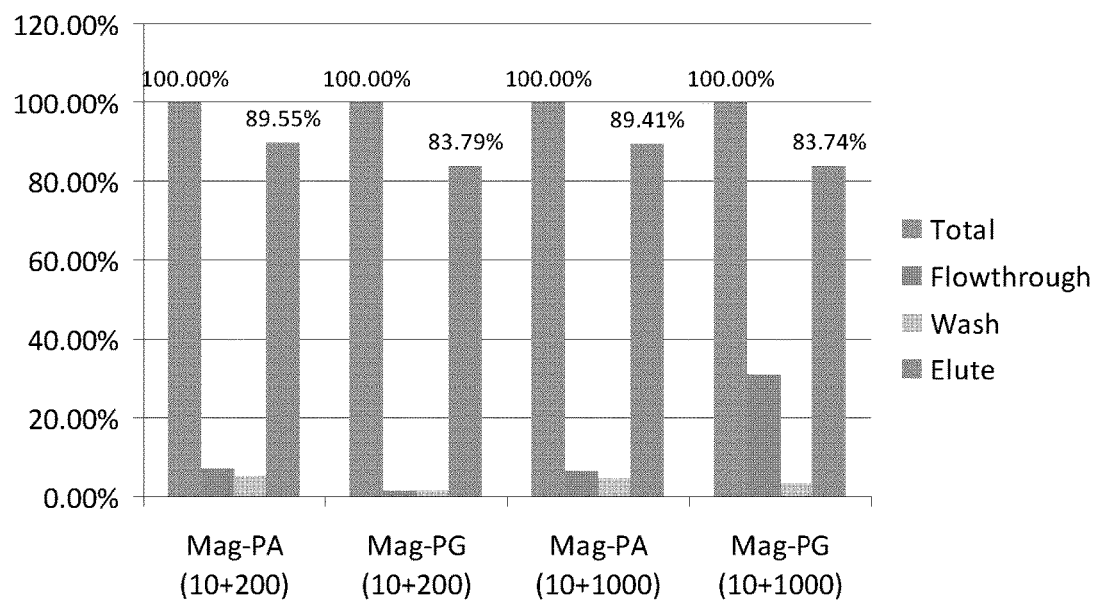

In another experiment, both the protein A nanocomposition and the protein G nanocomposition were used to separate an antibody. 10 ul nanocompositions were used to separate either 200 ng or 1000 ng antibody in the sample. The separation was carried out in a similar procedure as described above. As shown in FIG. 10, both protein A and protein G magnetic nanocompositions successfully separated the antibody from the sample, with a general recovery rate of above 80%.

Example 5. Purification of EP20 Antibody

The magnetic porous nanostructures as prepared in Example 3 were operably linked to Protein A, as described in Example 4.

Figure 11:
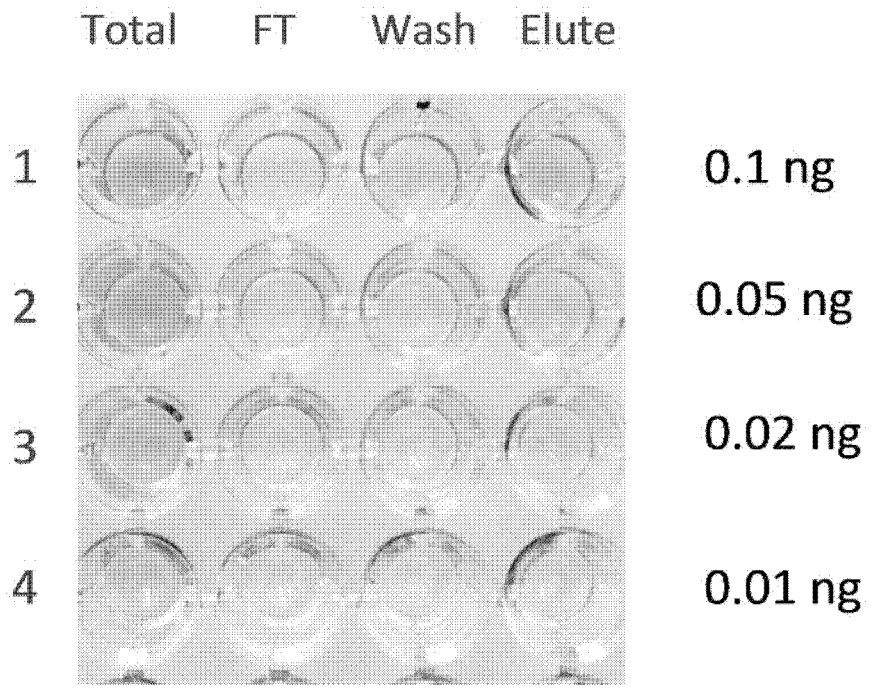
FIG. 11. Magnetic nanostructure-Protein A conjugates show high binding specificity and sensitivity to EP20 antibody. After EP 20 antibody is eluted from the binding of Protein A in an elution solution, the solution is transferred to a vial. ELISA (enzyme linked immunosorbent assay) test is then used to measure the presence and amount of EP20 antibodies.

The nanocompositions were purified, re-dispersed in 100 µl of PBS-T, and incubated with different amount of EP20 antibody (namely, 0.1 ng in Sample 1, 0.05 ng in Sample 2, 0.02 ng in Sample 3, and 0.01 ng in Sample 4), using the same procedure as described in Example 4. The incubated nanocomposition was separated from the sample using a magnet, washed and then eluted. The flowthrough, the wash, and the elute solutions were collected, and tested with ELISA as described above. A photograph of the ELISA plate was shown in FIG. 11. The results indicated that, the EP20 antibody, although at below an amount below 1 ng, was successfully separated from the sample and eluted in the eluate. The presence of the antibody in the flowthrough or the wash was not obvious.

Example 6. Purification of Rabbit Antibody

The magnetic porous nanostructures as prepared in Example 3 were operably linked to Protein A, as described in Example 4.

Figure 12:
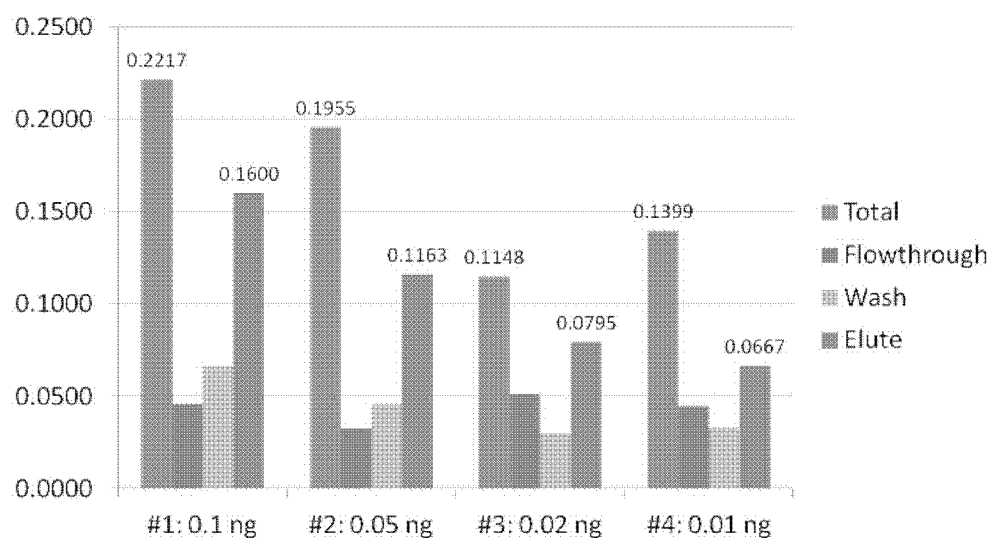
FIG. 12. Magnetic nanostructure-Protein A conjugates show high recovery rates for EP20 antibody that specifically binds to Protein A. The horseradish Peroxidase reaction time is 20 minutes. The recovery rates for EP20 antibodies are 72%, 59%, 69% and 48%, relative to 0.1 ng (sample 1#), 0.05 ng (sample 2#), 0.02 ng (sample 3#), and 0.01 ng (sample 4#) of EP20 antibodies respectively. The overall recovery rate is about or more than 50%, even when only 0.01 ng of EP20 antibodies are in solution.
Figure 13:
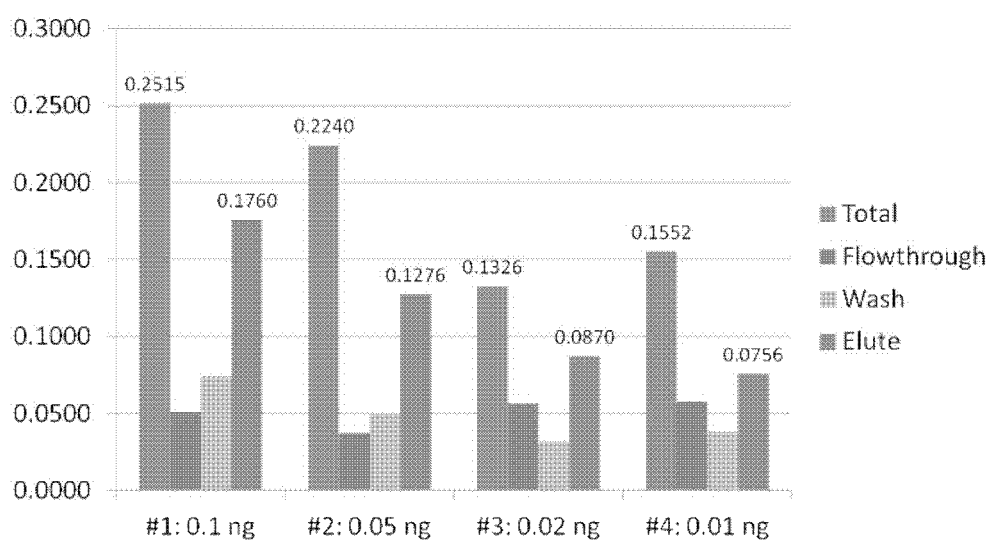
FIG. 13. Magnetic nanostructure-Protein A conjugates show high recovery rates for EP20 antibody that specifically binds to Protein A. The horseradish Peroxidase reaction time is 30 minutes. The recovery rates for EP20 antibodies are 70%, 73%, 66% and 49%, relative to 0.1 ng (sample 1#), 0.05 ng (sample 2#), 0.02 ng (sample 3#), and 0.01 ng (sample 4#) EP20 antibodies respectively. The overall recovery rate is about or more than 50%, even when only 0.01 ng of EP20 antibodies are in solution.

The nanocompositions were purified, re-dispersed in 100 µl of PBS-T, and incubated with different amount of rabbit antibody (namely, 0.1 ng in Sample 1, 0.05 ng in Sample 2, 0.02 ng in Sample 3, and 0.01 ng in Sample 4), using the same procedure as described in Example 4. The incubated nanocomposition was separated from the sample using a magnet, washed and then eluted. The flowthrough, the wash, and the elute solutions were collected, and tested with ELISA as described above. These solutions were measured at 640 nm for absorbance, and the results were shown in FIGS. 12 and 13. The results indicated that, the rabbit antibody, although at an amount below 1 ng, was successfully separated from the sample and eluted in the eluate. The recovery rate for the antibody at such a low amount was found to be at least 50%, and even higher.

Example 7. Purification of Rabbit Antibody in a Low Amount

The magnetic porous nanostructures as prepared in Example 3 were operably linked to Protein A, as described in Example 4.

Figure 14:
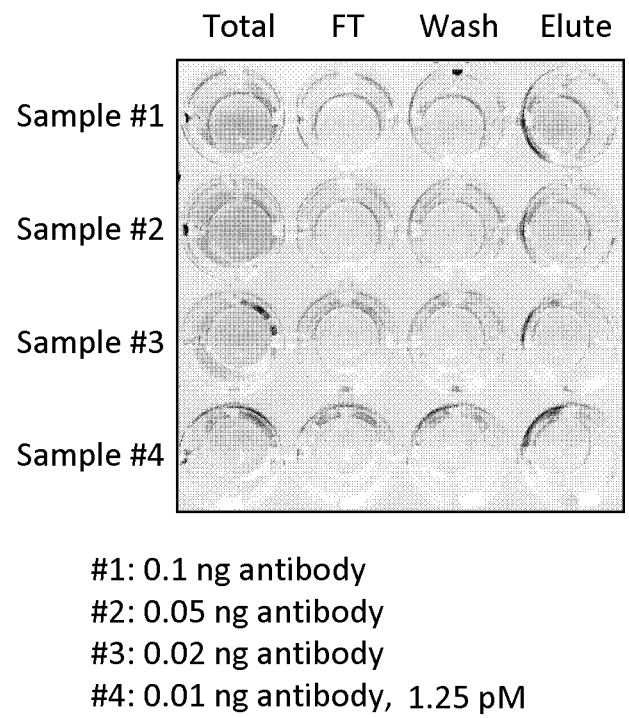
FIG. 14. Magnetic nanostructure-Protein A conjugates show high sensitivity and recovery rates for rabbit antibody that specifically binds to Protein A. 10 ul of Magnetic-Protein A Nanoparticles was mixed with 0.1, 0.05, 0.02, or 0.01 ng antibody in 50 ul total volume. The overall recovery rate is higher than 50%, even when only 0.01 ng (1.25 pM) of rabbit antibodies are in solution.
Figure 14:
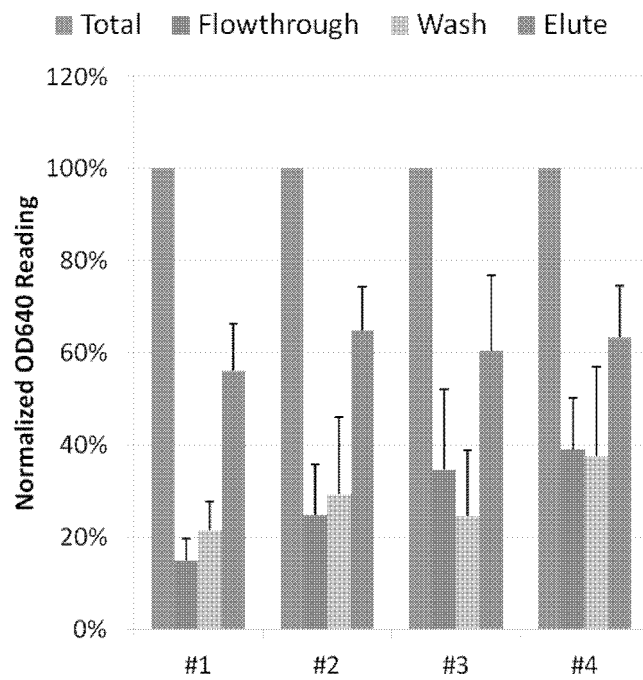

The nanocomposition was were purified, re-dispersed in 10 µl of PBS-T, and incubated with different amount of rabbit antibody (namely, 0.1 ng in Sample 1, 0.05 ng in Sample 2, 0.02 ng in Sample 3, and 0.01 ng (1.25 pM)) in Sample 4), in a total volume of 50 µl, using the same procedure as described in Example 4. The incubated nanocomposition was separated from the sample using a magnet, washed and then eluted. The flowthrough, the wash, and the elute solutions were collected, and tested with ELISA as described above. These solutions were measured at 640 nm for absorbance, and the results were shown in FIG. 14. The results indicated that, the rabbit antibody, although at below an amount below 1 ng and in a picomolar concentration, was successfully separated from the sample and eluted in the eluate. The recovery rate for the antibody at such a low amount was found to be at least 50%, and even higher.

Figure 15:
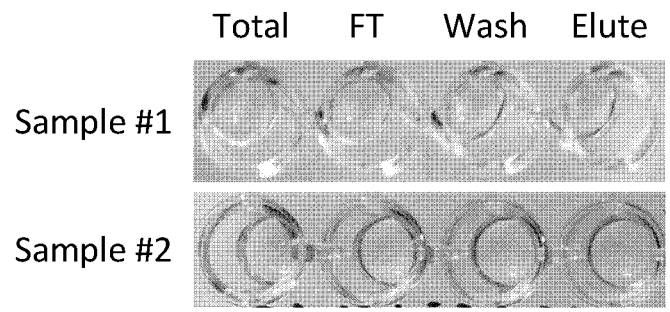
FIG. 15. Magnetic nanostructure-Protein A conjugates show high sensitivity for rabbit antibody that specifically binds to Protein A. 10 ul of Magnetic-Protein A Nanoparticles was mixed with 0.01 ng antibody in 1.5 ml or 10 ml volume (corresponding to 41.7 fM or 6.25 fM in concentration).
Figure 15:
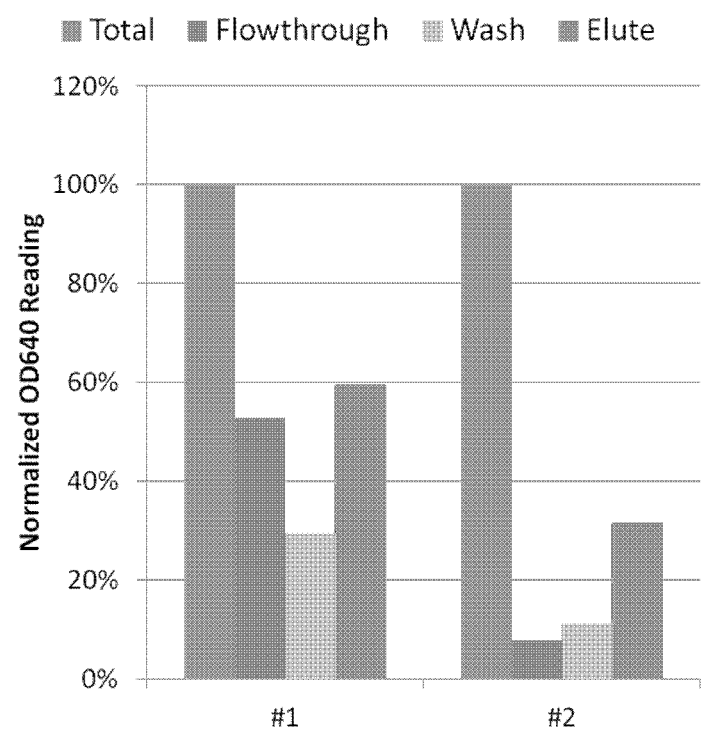

In another experiment, the nanocomposition was were purified, re-dispersed in 10 µl of PBS-T, and incubated with 0.01 ng of rabbit antibody in 1.5 ml (41.7 fM, Sample 1) or 10 ml volume (6.25 fM, Sample 2), using the same procedure as described in Example 4. The incubated nanocomposition was separated from the sample using a magnet, washed and then eluted. The flowthrough, the wash, and the elute solutions were collected, and tested with ELISA as described above. These solutions were measured at 640 nm for absorbance, and the results were shown in FIG. 15. The results indicated that, the rabbit antibody, although at an amount below 1 ng and in a femtomolar level, was successfully separated from the sample and eluted in the elute. The recovery rate for the antibody at such a low amount demonstrated the high sensitivity of the method.

Example 8. Selection of a Desired Population of Cells

Figure 16:
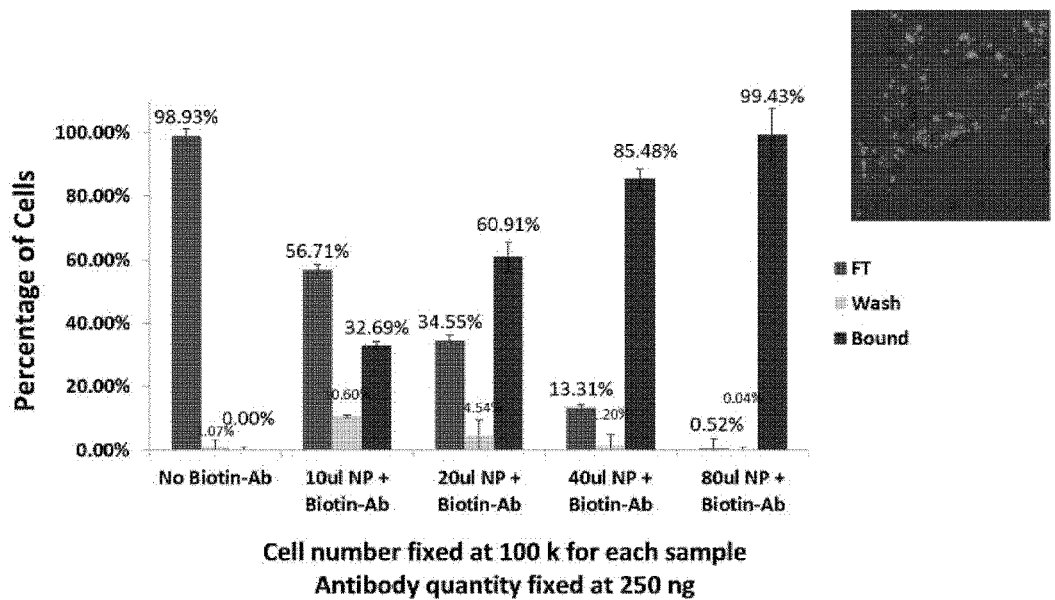
FIG. 16. Capture of target cells is enhanced with an increased amount of nanoparticles although the analyte binding member remains in constant amount. Different percentage of cells have been captured by fixing cell number at 100 k and antibody quantity at 250 ng. It indicates that the percentage of bound cells increases with the number of magnetic nanoparticles. In another words, the magnetic nanoparticles can be used to select a desired population of cells by adjusting the ratio of the number of the magnetic beads to the cells. For example, this property could be used to select antibody high producer cells, or specific cells with a low thresh-hold of number of markers on surface.

Fluorescent magnetic nanoparticles were conjugated with streptavidin, and mixed with biotinylated antibody. A constant amount of 250 ng antibody was mixed with different amounts of the nanoparticles, i.e., at 10 ul, 20 ul, 40 ul, and 80 ul, to prepare four different test compositions. Then the four test compositions were added respectively to four samples, each with a fixed cell number of 100 000 cells expressing the antigen. The cells were incubated with the test compositions to allow capture of the cells by the antibody on the nanoparticles, and then were separated by flowing through a magnetic grid. The magnetic grid was washed with PBS, and then eluted with an eluting buffer. The solution obtained after flowthrough ("FT"), washing ("Wash") and eluting ("Bound") were collected respectively, and detected for the amount of cells (see FIG. 16). The percentage of captured cells increased with the increase in the amount of the magnetic nanoparticles, although the amount of the antibody remained the same. The percentage of the cells was up to 99.43% when 80 µl of magnetic nanoparticles was used, whereas when 10 µl of magnetic nanocomposition was added to the sample, the percentage of captured cells was 32.69%.

Figure 17:
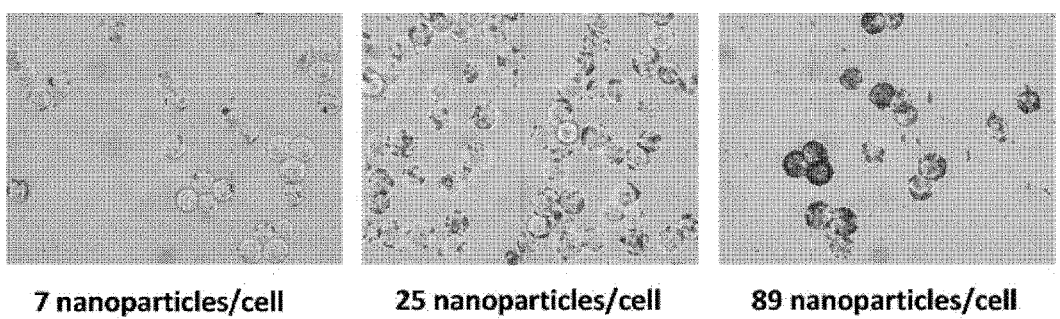
FIG. 17 shows bright field images of three samples with different number of nanoparticles per cell. It indicates that the number of nanoparticles per cell can be controlled by the starting ratio of the number of nanoparticles to the number of cells before incubation. These figures show the cells tagged with different average number of beads. These cells are magnetically captured to the side of a vial using a magnet, then re-dispersed in cell medium and imaged under microscope.

The number of nanoparticles per cell could be controlled by the starting ratio of the number of nanoparticles to cells before incubation. Cells were mixed with magnetic nanoparticles at different ratios, namely, 7 nanoparticles/cell, 25 nanoparticles/cell, and 89 nanoparticles/cell. These cells were magnetically captured to the side of a vial using a magnet, and then re-dispersed in cell medium and imaged under microscope. As shown in FIG. 17, by adjusting the starting ratio of the number of nanoparticles to cells, the bright field images showed the cells were tagged with different average number of beads. The cells of desired number of nanoparticle per cell are selected to represent a high presence or expression of the analyte.

Example 9. Purification and Labelling of Cells

Figure 18:
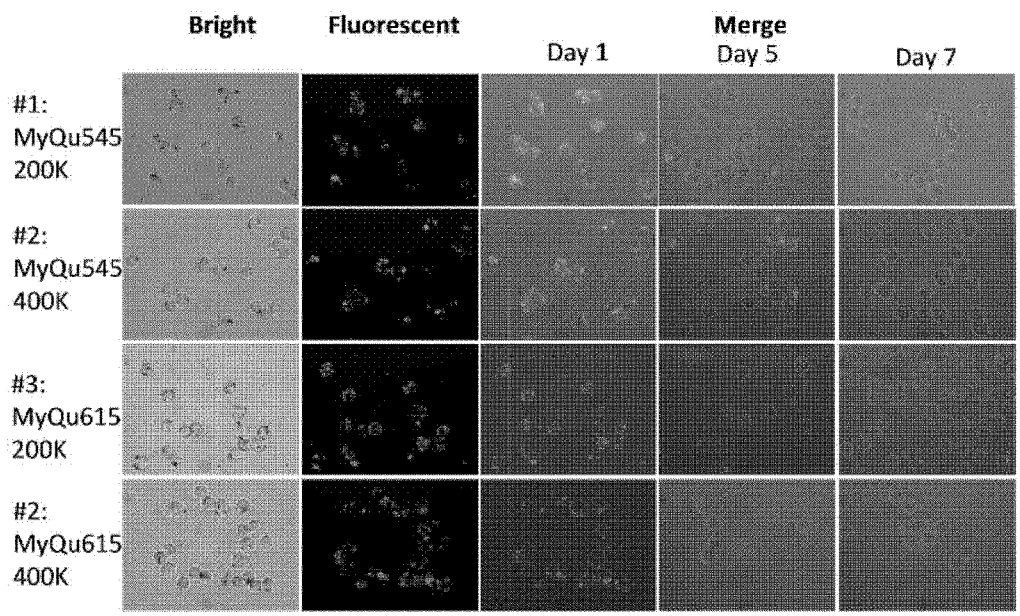
FIG. 18 shows fluorescent magnetic nanoparticles for high capacity cell purification and concurrent labeling. The nanoparticles are streptavidin coated, then conjugated with biotinlyated-EpCAM antibody. Cell lines used are human breast cancer cell MCF-7. Cells are tagged with nanoparticles, as cells divide, number of nanoparticle per cell decreases, after 5-7 days, majority of cells contain no nanoparticles.

Fluorescent magnetic nanoparticles were coated with streptavidin and then conjugated with biotinlyated-EpCAM antibody. Cell lines used here were human breast cancer cell MCF-7. As shown in FIG. 18, the cells were tagged with nanoparticles, as cells divided, the number of nanoparticles per cell decreased. After 5-7 days, majority of cells contained no nanoparticles.

Example 10. Recovery of Low Number of Cancer Cells Spiked

Figure 19:
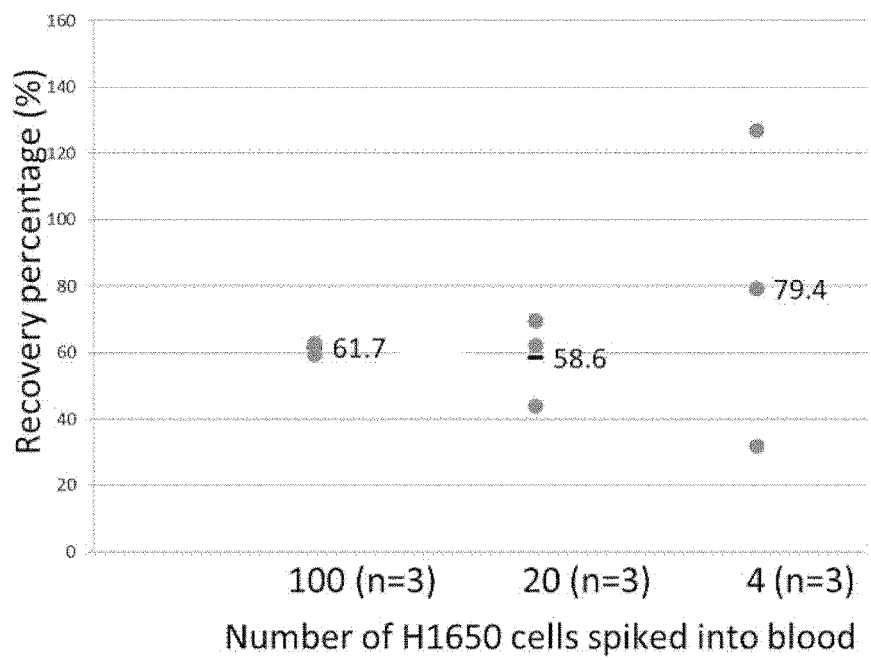
FIG. 19 shows magnetic nanoparticles can be used to capture and identify circulating tumor cells from whole blood samples. The recovery efficiency is high even for low number of cancer cells spiked into whole blood. The H1650 cells are used to evaluate the recovery efficiency herein.
Figure 20:
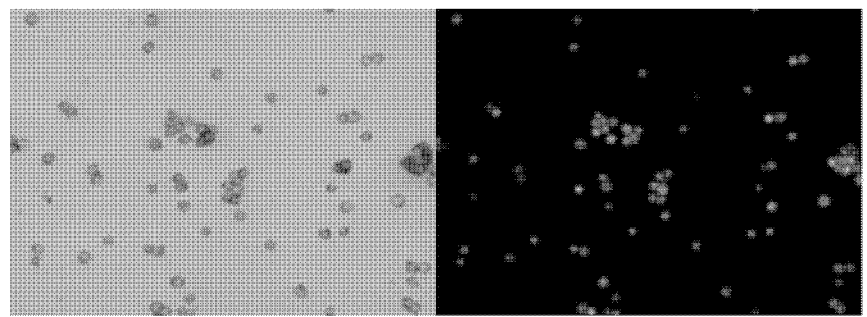
FIG. 20 shows purity of magnetically separated cancer cells from whole blood samples is almost 100%. The left figure shows the bright field image of magnetically separated 400 k H1650 cells from whole blood. The right figure shows the corresponding fluorescent cell image by pre-labeling these cells with CFSE staining.

Fluorescent magnetic nanoparticles were coated with streptavidin and then conjugated with biotinlyated-EpCAM antibody. 100, 20 or 4 H1650 cells prestained with CFSE of green fluorescence were spiked into 1 ml whole blood. The blood sample spiked with the H1650 cells were incubated with the magnetic nanoparticles, followed by magnetic pull-down with a smallmagnet. After removing the supernatant, the separated cells were redispersed in medium and counted. As shown in FIG. 19, the recovery efficiency was high even for low number of spiked H1650 cells.

In another experiment, 400,000 H1650 cells pre-labeled with CFSE of green fluorescence were recovered from whole blood samples, using magnetic nanoparticles. As shown in FIG. 18, for each cell shown in the bright field image (left), there is a corresponding florescent cell image (right), indicating that the cells recovered from the whole blood are in high purity (almost 100%).

The invention claimed is:

1. A method of capturing, enriching, purifying, detecting or measuring an analyte in a sample at a sub-nanogram level, comprising the steps of
   a) providing a nanocomposition comprising:
      a nanostructure having magnetic property, and an analyte-capturing member,
         wherein the nanostructure is operably linked to the analyte-capturing member,
         wherein the nanostructure comprises a nanoparticle and a low density porous 3-D structure, wherein the low density porous 3-D structure is made of organosilane, and has a density of <1.0 g/cc determined from dry mass of the 3-D structure divided by the total volume of such 3-D structure in an aqueous solution, wherein the nanoparticle is embedded in the low density porous 3-D structure,
   wherein the nanocomposition is capable of capturing an analyte at a concentration of no more than 1 nM, and the analyte is an antibody, a protein/peptide or a nucleic acid,
   b) contacting the sample with the nanocomposition to form a mixture solution and allowing the binding of the analyte with the nanocomposition,
   c) applying a magnetic field to the mixture, and
   d) evaluating the presence of or absence of the analyte.

2. The method of claim 1 further comprising a step of removing liquid from the mixture solution in the presence of the magnetic field.

3. The method of claim 1 further comprising a step of washing the nanocomposition in the presence of magnetic field after removing the liquid and before eluting.

4. The method of claim 1 further comprising a step of eluting the analyte from the nanocomposition, and collecting the analyte from the nanocomposition in the presence of a magnetic field.

5. The method of claim 1 further comprising a step of analyzing the eluate by detecting the presence of the analyte or quantifying the amount of the analyte.

6. The method of claim 1, further comprising determining and applying a ratio of the nanocomposition to the analyte and mixing the nanocomposition with the sample based on the ratio.

7. The method of claim 1, further comprising evaluating the bounded nanocompositions to each said analyte and selecting the analyte binding to a desired number of nanocompositions.

* * * * *